United States Patent
Lee et al.

(10) Patent No.: US 10,542,949 B2
(45) Date of Patent: Jan. 28, 2020

(54) X-RAY APPARATUS AND SYSTEM

(71) Applicant: SAMSUNG ELECTRONICS CO., LTD., Suwon-si (KR)

(72) Inventors: Byeong-won Lee, Suwon-si (KR); Jeong-yong Song, Bucheon-si (KR); Do-kwan Oh, Suwon-si (KR); Hyun-hwa Oh, Hwaseong-si (KR); Choong-hwan Choi, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/204,480

(22) Filed: Nov. 29, 2018

(65) Prior Publication Data

US 2019/0110768 A1    Apr. 18, 2019

Related U.S. Application Data

(63) Continuation of application No. 15/218,455, filed on Jul. 25, 2016, now Pat. No. 10,172,578.

(30) Foreign Application Priority Data

Jul. 23, 2015 (KR) .................. 10-2015-0104359
Jul. 13, 2016 (KR) .................. 10-2016-0088711

(51) Int. Cl.
*A61B 6/08* (2006.01)
*A61B 6/00* (2006.01)

(52) U.S. Cl.
CPC ............. *A61B 6/4417* (2013.01); *A61B 6/08* (2013.01); *A61B 6/463* (2013.01); *A61B 6/52* (2013.01); *A61B 6/54* (2013.01); *A61B 6/4452* (2013.01); *A61B 6/4464* (2013.01); *A61B 6/587* (2013.01)

(58) Field of Classification Search
CPC ....... A61B 6/08; A61B 6/4417; A61B 6/4452; A61B 6/4464; A61B 6/463; A61B 6/52; A61B 6/54; A61B 6/587
See application file for complete search history.

(56) References Cited

U.S. PATENT DOCUMENTS

| | | | |
|---|---|---|---|
| 6,088,424 | A | 7/2000 | Postlethwaite et al. |
| 6,267,503 | B1 | 7/2001 | McBride |
| 7,477,723 | B2 | 1/2009 | Kamegawa et al. |
| 8,419,276 | B2 | 4/2013 | Oda et al. |
| 8,542,248 | B2 | 9/2013 | Goto |
| 2002/0067793 | A1 | 6/2002 | Stierstorfer |

(Continued)

FOREIGN PATENT DOCUMENTS

| | | |
|---|---|---|
| JP | 2006-204329 A | 8/2006 |
| JP | 2010-51737 A | 3/2010 |

(Continued)

OTHER PUBLICATIONS

Communication dated Mar. 1, 2017, issued by the European Patent Office in counterpart European Patent Application No. 16180815.9.

(Continued)

*Primary Examiner* — Mark R Gaworecki
(74) *Attorney, Agent, or Firm* — Sughrue Mion, PLLC

(57) ABSTRACT

An X-ray apparatus performs image processing on an image of an object photographed by using a camera, and uses the image-processed image as an image marker in an X-ray image. A display is configured to display the X-ray image and the image marker on the region of the X-ray image.

15 Claims, 31 Drawing Sheets

(56) References Cited

U.S. PATENT DOCUMENTS

| | | |
|---|---|---|
| 2004/0254456 A1 | 12/2004 | Ritter |
| 2005/0013410 A1 | 1/2005 | Hornegger |
| 2009/0136000 A1 | 5/2009 | Nishii et al. |
| 2009/0141958 A1 | 6/2009 | Graumann et al. |
| 2011/0129058 A1 | 6/2011 | Ulrici et al. |
| 2013/0077745 A1 | 3/2013 | Wang et al. |
| 2014/0016750 A1 | 1/2014 | Kang et al. |
| 2014/0241497 A1 | 8/2014 | Keall et al. |
| 2015/0003674 A1 | 1/2015 | Eun et al. |
| 2015/0339521 A1 | 11/2015 | Chen et al. |

FOREIGN PATENT DOCUMENTS

| | | |
|---|---|---|
| JP | 4665774 B2 | 4/2011 |
| JP | 2012-147978 A | 8/2012 |
| JP | 2012-187142 A | 10/2012 |
| JP | 2014-23592 A | 2/2014 |
| JP | 2014-198271 A | 10/2014 |
| JP | 2015-77251 A | 4/2015 |
| WO | 2015081295 A1 | 6/2015 |

OTHER PUBLICATIONS

Communication dated Nov. 28, 2016, issued by the European Patent Office in counterpart European application No. 16180815.9.
Communication dated Mar. 21, 2019, issued by the European Patent Office in counterpart European Application No. 18204140.0.

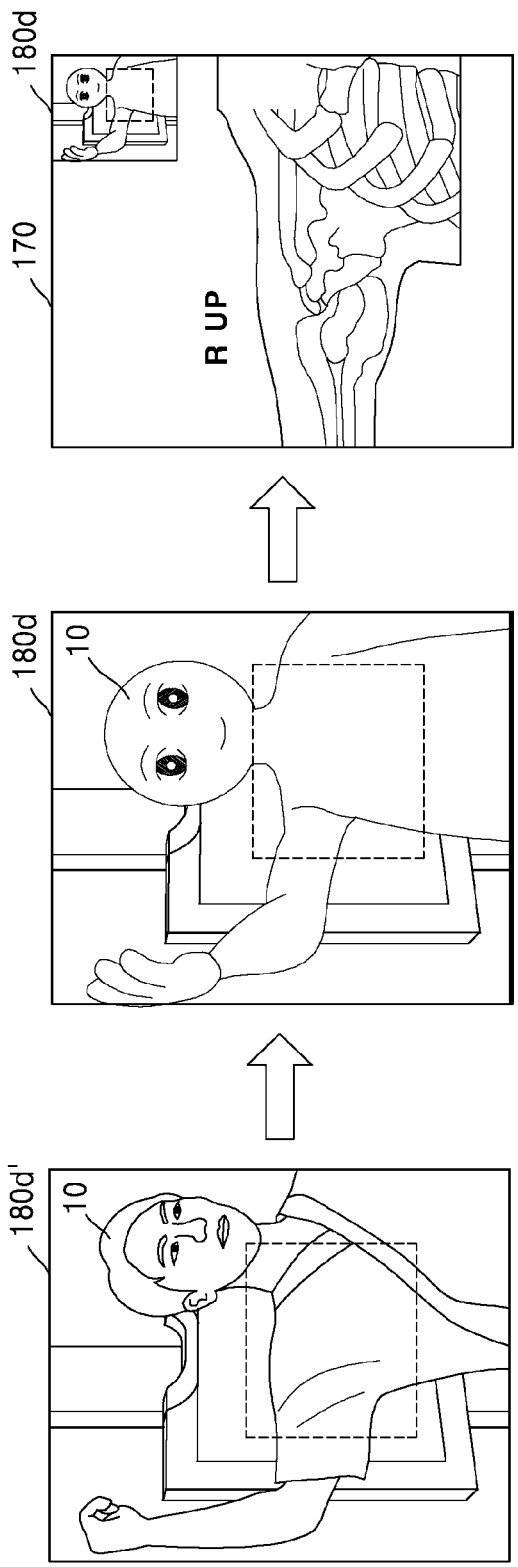

X-RAY APPARATUS AND SYSTEM

CROSS-REFERENCE TO RELATED APPLICATIONS

This is a continuation of U.S. application Ser. No. 15/218,455 filed Jul. 25, 2016, which claims priority from Korean Patent Application No. 10-2015-0104359, filed on Jul. 23, 2015, and Korean Patent Application No. 10-2016-0088711, filed on Jul. 13, 2016, in the Korean Intellectual Property Office, the disclosure of which are incorporated herein in their entireties by reference.

BACKGROUND

1. Field

Apparatuses consistent with embodiments relate to X-ray apparatuses and systems, and more particularly, to X-ray apparatuses and systems that may obtain an image of an object photographed by using a camera attached to the X-ray apparatuses and may use the obtained image to capture an X-ray image.

2. Description of the Related Art

The X-rays are electromagnetic waves having wavelengths ranging from 0.01 to 100 Å, and may pass through an object and thus are widely used in medical devices for imaging the inside of a living body or are used as non-destructive testing devices in the industry.

An X-ray apparatus using X-rays may obtain an X-ray image of an object by transmitting X-rays emitted from an X-ray source through the object and detecting a strength difference between the transmitted X-rays by using an X-ray detector. Accordingly, an internal structure of the object may be detected and the object may be diagnosed by using the X-ray image. The X-ray apparatus easily detects the inner structure of the object by using the fact that transmittances of the X-rays vary according to a density of the object and atomic numbers of atoms constituting the object.

SUMMARY

One or more embodiments may provide X-ray apparatuses and systems that perform image processing on an image of an object photographed by using a camera attached to the X-ray apparatuses and use the image-processed image as an image marker on an X-ray image.

One or more embodiments may provide X-ray apparatuses and systems that control a position of a mechanical device of the X-ray apparatuses by performing image processing on an image of an object photographed by using a camera attached to the X-ray apparatuses.

One or more embodiments may provide X-ray apparatuses and systems that control an imaging condition of the X-ray apparatuses by performing image processing on an image of an object photographed by using a camera attached to the X-ray apparatuses.

According to an aspect of another embodiment, an X-ray apparatus for obtaining an X-ray image of an object by X-ray imaging the object includes: an X-ray source configured to emit X-rays to the object; an image obtainer attached to the X-ray source and configured to obtain a representative still image of the object; an X-ray detector configured to receive X-rays transmitted through the object to obtain an X-ray image of the object; a controller configured to generate an image marker by applying image processing to the representative still image obtained by the image obtainer and to generate the X-ray image; and an image output unit configured to display the image marker so that the image marker overlaps a first region of the X-ray image.

The image obtainer may be further configured to obtain a plurality of still images of the object by photographing the object, the representative still image is an image that represents a candidate body part of the object, among the plurality of still images, and the candidate body part is a part of the object to be X-rayed.

The representative still image may be a still image obtained by photographing the object immediately prior to capturing the X-ray image of the object.

The controller may be further configured to adjust a direction in which the representative still image is displayed on the image display.

The controller may be further configured to adjust the direction in which the representative still image is displayed based on a certain direction information.

The controller may be further configured to adjust the direction in which the representative still image is displayed by using a geometric information of the X-ray apparatus and an image algorithm.

The image marker may include a same image as the representative still image.

The controller may be further configured to generate the image marker by performing the image processing that blurs or mosaics the representative still image.

The controller may be further configured to generate the image marker by performing the image processing that transforms the representative still image into a cartoon image.

The controller may be further configured to detect a shape of a candidate body part of the object by performing the image processing on the representative still image, select a pre-stored image similar to the detected shape of the candidate body part of the object, and generate the selected pre-stored image as the image marker, and the candidate body part may be a part of the object to be X-rayed.

The controller may be further configured to generate a guide image indicating a direction or a positional relationship of the object in the image marker.

The guide image may include at least one among an illustration, a cartoon image, a figure image, and a text.

The region of the X-ray image may be determined based on a certain information related to a candidate body part of the object, and the candidate body part may be a part of the object to be X-rayed.

The controller may be further configured to detect a clinical information by performing the image processing on the X-ray image, and determine the region, to overlap with the image marker, whose clinical information in the X-ray image is determined to be relatively minor, as compared to other regions of the X-ray image.

According to another aspect of another embodiment, a method of photographing an object by using an X-ray apparatus and obtaining an X-ray image of the object includes: obtaining a representative still image of the object by photographing the object; generating an image marker by performing image processing on the representative still image; and obtaining the X-ray image of the object and displaying the image marker on the X-ray image so that the image marker overlaps a region of the X-ray image.

The obtaining the representative still image may include: obtaining a plurality of still images of the object by photographing the object; and selecting the representative still image that represents a candidate body part of the object, among the plurality of still images, and wherein the candidate body part is a part of the object to be X-rayed.

The representative still image may be a still image, among the plurality of still images, obtained by photographing the object immediately prior to capturing the X-ray image of the object.

The method may further include adjusting a direction in which the representative still image is displayed, after the selecting the representative still image.

The adjusting the direction of the representative still image may include: adjusting the direction of the representative still image based on a direction information preset in the X-ray apparatus.

The adjusting the direction of the representative still image may include: adjusting the direction of the representative still image by using a geometric information of the X-ray apparatus and an image algorithm.

The image marker may include a same image as the representative still image.

The generating the image marker may include: generating the image marker by performing the image processing that blurs or mosaics the representative still image.

The generating the image marker may include generating the image marker by performing the image processing that transforms the representative still image into a cartoon image.

The generating the image marker may include: detecting a shape of a candidate body part of the object by performing the image processing on the representative still image; selecting a pre-stored image similar to the detected shape of the candidate body part of the object, among images pre-stored in the X-ray apparatus; and generating the selected pre-stored image as the image marker, wherein the candidate body part is a part of the object to be X-rayed.

The method may further include generating a guide image indicating a direction or a positional relationship of the object in the image marker.

The guide image may include at least one among an illustration, a cartoon image, a figure image, and a text.

The region of the X-ray image may be determined based on a certain information of a candidate body part of the object, and the candidate body part may be a part of the object to be X-rayed.

The displaying the image marker may include: detecting clinical information by performing the image processing on the X-ray image; and determining the region, to be overlapped with the image marker, whose clinical information in the X-ray image is determined to be relatively minor, as compared to other regions of the X-ray image.

According to another aspect of another embodiment, a non-transitory computer-readable recording medium has recorded thereon a program which, when executed by a computer system, causes the computer system to execute the method.

According to another aspect of another embodiment, an X-ray apparatus for controlling a position of an X-ray emitter includes: an image obtainer configured to obtain an image of an object by photographing the object; a controller configured to identify a candidate region of the object and a central point of the object by performing image processing on the obtained image, generate a thumbnail image by causing user interfaces (UIs) indicating an irradiation region shape of the X-ray emitter and a central point of the X-ray emitter to overlap the identified candidate region of the object and the identified central point of the object, the candidate region being a region of the object to be X-rayed, and calculate the irradiation region shape of the X-ray emitter and the position of the X-ray emitter by matching the candidate region of the object and the central point of the object with the irradiation region of the X-ray emitter and the central point of the X-ray emitter, respectively, and control the position of the X-ray emitter based on the matched irradiation region of the X-ray emitter and the matched central point of the X-ray emitter; and a display configured to display the thumbnail image.

A plurality of the irradiation regions of the X-ray emitter and a plurality of the central points of the X-ray emitter to be matched with the candidate region of the object and the central point of the object may be provided, and the controller may be further configured to generate a plurality of thumbnail images by causing each of the plurality of irradiation regions of the X-ray emitter and each of the plurality of central points of the X-ray emitter to overlap the obtained image.

The display may be further configured to display the plurality of thumbnail images, and the X-ray apparatus may further include: a user input receiver configured to receive a user input that selects one among the plurality of thumbnail images displayed on the display; and a driver configured to adjust the plurality of irradiation regions of the X-ray emitter and the position of the X-ray emitter based on the user input.

The user input receiver may include: a touch screen which is embodied in the display and configured to receive a touch input of a user that touches the one among the plurality of thumbnail images displayed on the display.

The controller may be configured to convert the candidate region of the object and the central point of the object into virtual graphical user interfaces (GUIs), and the display may be configured to display the virtual GUIs to overlap the obtained image.

The display may be further configured to display a UI that displays the central point of the object as a first marker and display the central point of the X-ray emitter as a second marker.

A position of the second marker may be corrected based on a user input.

The controller may be further configured to identify a user who uses the X-ray apparatus and obtains setting information about the irradiation region of the X-ray emitter and the central point of the X-ray emitter, and generate the thumbnail image based on the setting information corresponding to the identified user.

The X-ray apparatus may further include a storage device configured to store the setting information about the irradiation region of the X-ray emitter and the central point of the X-ray emitter that is input by the user, wherein the controller is further configured to obtain information about the irradiation region of the X-ray emitter and the central point of the X-ray emitter by analyzing the setting information stored in the storage device.

The controller may be further configured to generate the thumbnail image based on information about an imaging protocol for X-ray imaging the object.

According to another aspect of another embodiment, a method of controlling a position of an X-ray emitter includes: obtaining an image of an object by photographing the object; identifying a candidate region of the object and a central point of the object by performing image processing on the obtained image; calculating an irradiation region shape of the X-ray emitter and the position of the X-ray emitter by matching the identified candidate region of the object and the identified central point of the object with the irradiation region of the X-ray emitter and the central point of the X-ray emitter, respectively, the candidate region being a region of the object to be X-rayed; generating a thumbnail image by causing information about the calculated irradiation region shape of the X-ray emitter and the calculated position of the X-ray emitter to overlap the obtained image; and displaying the thumbnail image.

A plurality of the irradiation regions of the X-ray emitter and a plurality of the central points of the X-ray emitter to be matched with the candidate region of the object and the central point of the object may be provided, and the generating the thumbnail image may include generating a plurality of thumbnail images by causing each of the plurality of irradiation regions of the X-ray emitter and each of the plurality of central points of the X-ray emitter to overlap the obtained image.

The displaying the thumbnail image may include displaying the plurality of thumbnail images, and the method may further include: receiving a user input that selects one among the plurality of thumbnail images on the display; and adjusting the irradiation region of the X-ray emitter and the position of the X-ray emitter based on the user input.

The generating the thumbnail image may include: converting the candidate region of the object and the central point of the object into virtual graphics; and displaying a user interface (UI) so that the virtual graphics overlap the obtained image.

The displaying the thumbnail image may include: displaying a user interface (UI) that displays the central point of the object as a first marker and displays the central point of the X-ray emitter as a second marker.

A position of the second marker may be corrected based on a user input.

The generating the thumbnail image may include: identifying a user who uses the X-ray apparatus; and generating the thumbnail image based on setting information about the irradiation region of the X-ray emitter and the central point of the X-ray emitter that is provided by the identified user.

The generating the thumbnail image may include: generating the thumbnail image based on information about an imaging protocol for X-ray imaging the object.

According to another aspect of another embodiment, an X-ray apparatus includes: an image obtainer configured to photograph an examination room in which the X-ray apparatus is located or photograph an object and an ambient area around the object, and obtain an image of the photographed examination room or the photographed object and ambient area, respectively; and a controller configured to detect an X-ray imaging condition including at least one among a luminance of the examination room, luminances of the object and the ambient area, and colors of the object and the ambient area, by performing image processing on the obtained image, and change at least one among imaging option settings of the X-ray apparatus based on the detected X-ray imaging condition, the imaging option settings including a luminance setting of the examination room, a luminance setting of an X-ray irradiation region of the object, and a color setting of the X-ray irradiation region.

The image obtainer may include: a first camera attached to the examination room and configured to photograph a user who uses the X-ray apparatus and an entire examination room; and a second camera located on a side of a collimator and configured to photograph the X-ray irradiation region and the ambient area, of the object.

The X-ray apparatus may further include: a collimator which includes a light-emitting diode (LED) light source and is configured to adjust a region of the object to which X-rays are radiated.

The controller may be configured to detect a difference between the luminance of the examination room and a luminance of the X-ray irradiation region, and adjust a light source of the examination room or the LED light source of the collimator based on the difference between the luminance of the examination room and the luminance of the X-ray irradiation region.

The controller may be configured to adjust a color or a brightness of the LED light source based on the detected color of the object and the detected color of the ambient area around the object.

The controller may be further configured to detect a position of the user by performing the image processing on an image of the user obtained by photographing the user with the first camera, and adjust the luminance of the examination room based on the detected position of the user.

The first camera may be configured to obtain an image of the user by photographing the user who performs an action, the action being a user action of manipulating a collimator to adjust the X-ray irradiation region of the object, and the controller may be further configured to detect the action of the user by performing the image processing on the obtained image of the user, and adjust a luminance or a color of a light source of the collimator based on the detected action of the user.

According to another aspect of another embodiment, an X-ray imaging method includes: obtaining an image of an examination room in which an X-ray apparatus is located or of an object and an ambient area around the object by photographing the examination room or the object and the ambient area, respectively; detecting an X-ray imaging condition including at least one among a luminance of the examination room, luminances of the object and the ambient area, and colors of the object and the ambient area, by performing image processing on the obtained image; and changing at least one among imaging option settings of the X-ray apparatus based on the detected X-ray imaging condition, the imaging option settings including a luminance setting of the examination room, a luminance setting of an X-ray irradiation region of the object, and a color setting of the X-ray irradiation region.

The detecting the X-ray imaging condition may include detecting a difference between the luminance of the examination room and the luminance of the X-ray irradiation region of the object, and the changing the at least one among the imaging option settings of the X-ray apparatus may include adjusting a light source of the examination room or a light source of a collimator based on the difference between the luminance of the examination room and the luminance of the X-ray irradiation region.

The detecting the X-ray imaging condition may include detecting a position of a user included in the obtained image by performing the image processing on the obtained image of the examination room, and the changing the at least one among the imaging option settings of the X-ray apparatus may include adjusting the luminance of the examination room based on the detected position of the user.

The obtaining the image may include obtaining an image of a user by photographing the user who performs an action, the detecting the X-ray imaging condition may include detecting the action of the user by performing the image processing on the obtained image, the action being a user action of manipulating a collimator for adjusting the X-ray irradiation region of the object, and the changing the at least one among the imaging option settings of the X-ray apparatus may include changing a luminance or a color of a light source of the collimator based on the detected action of the user.

BRIEF DESCRIPTION OF THE DRAWINGS

The above and/or other aspects will become more apparent by describing certain embodiments with reference to the accompanying drawings, in which:

FIGS. 7A, 7B, 7C, and 7D are views for explaining an image processing method of generating an image marker by using a representative still image according to an embodiment;

DETAILED DESCRIPTION

Figure 1:
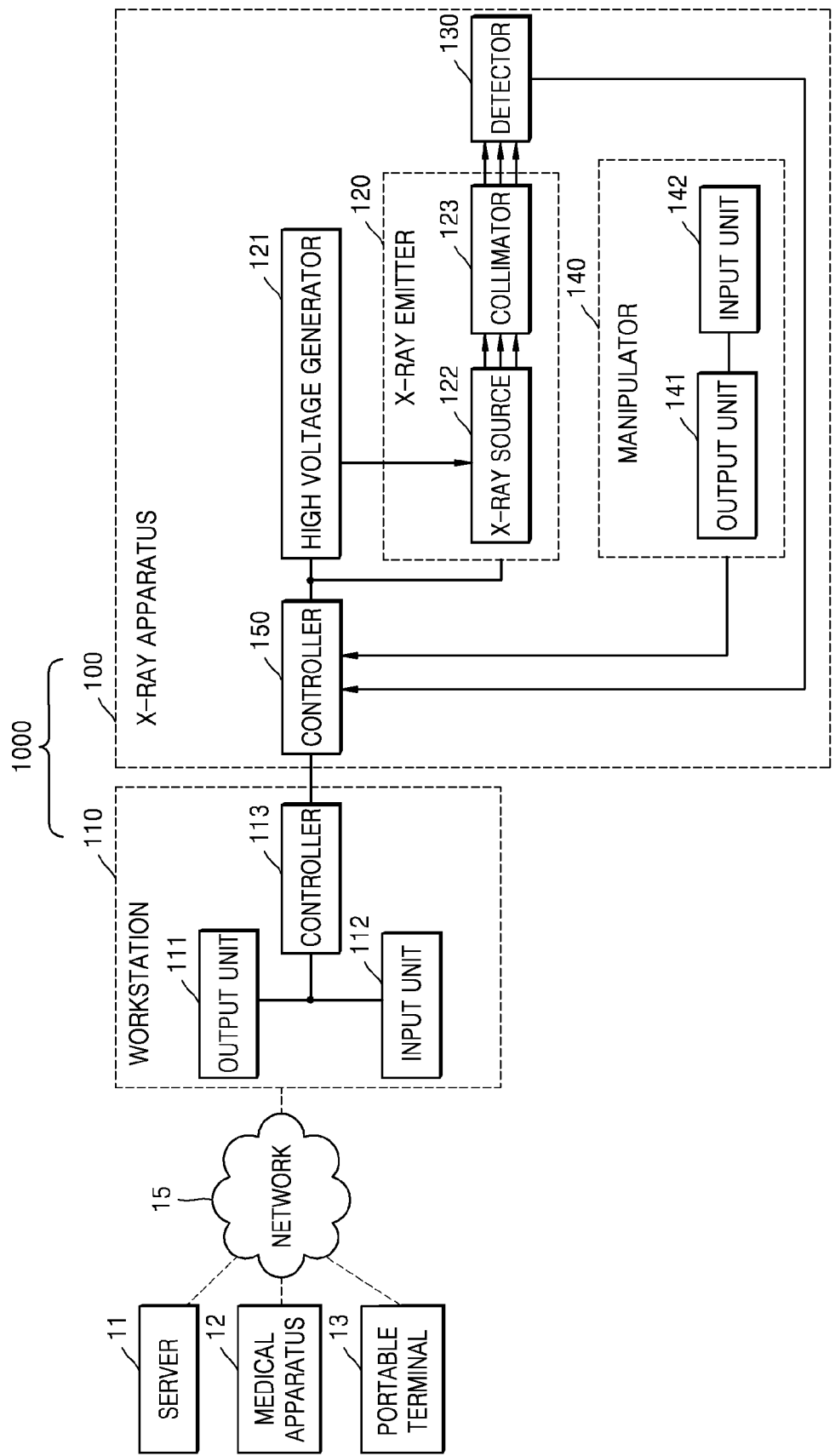
FIG. 1 is a block diagram illustrating a configuration of an X-ray system.

Certain embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the embodiments. However, it is apparent that the embodiments can be practiced without those specifically defined matters. Also, well-known functions or constructions are not described in detail since they would obscure the description with unnecessary detail.

The terms used in this specification are those general terms currently widely used in the art in consideration of functions regarding the present disclosure, but the terms may vary according to the intention of those of ordinary skill in the art, precedents, or new technology in the art. Also, specified terms may be selected by the applicant, and in this case, the detailed meaning thereof will be described in the detailed description of the inventive concept. Thus, the terms used in the specification should be understood not as simple names but based on the meaning of the terms and the overall description of the inventive concept.

Throughout the specification, an "image" may denote multi-dimensional data composed of discrete image elements (for example, pixels in a two-dimensional (2D) image and voxels in a three-dimensional (3D) image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.

In addition, an "object" may be a human, an animal, or a part of a human or animal. For example, the object may include an organ (for example, the liver, the heart, the womb, the brain, breasts, or the abdomen), blood vessels, or a combination thereof. The object may be a phantom. The phantom denotes a material having a volume, a density, and an effective atomic number that are approximately the same as those of a living organism. For example, the phantom may be a spherical phantom having similar properties to those of the human body.

Throughout the specification, a "user" may be, but is not limited to, a medical expert, for example, a medical doctor, a nurse, a medical laboratory technologist, or a medical imaging expert, or a technician who repairs medical apparatuses.

An X-ray apparatus is a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in simple chest imaging, simple abdomen imaging, simple skeleton imaging, simple nasal sinuses imaging, simple neck soft tissue imaging, and breast imaging.

FIG. 1 is a block diagram of an X-ray system 1000. Referring to FIG. 1, the X-ray system 1000 includes an X-ray apparatus 100 and a workstation 110. The X-ray apparatus 100 shown in FIG. 1 may be a fixed-type X-ray apparatus or a mobile X-ray apparatus. The X-ray apparatus 100 may include an X-ray emitter 120, a high voltage generator 121, a detector 130, e.g., an X-ray detector, a manipulator 140, and a controller 150, e.g., a microprocessor. The controller 150 may control overall operations of the X-ray apparatus 100.

The high voltage generator 121 generates a high voltage for generating X-rays, and applies the high voltage to an X-ray source 122, i.e., an X-ray tube.

The X-ray emitter 120 includes the X-ray source 122 for receiving the high voltage from the high voltage generator 121 to generate and radiate an X-ray, and a collimator 123 for guiding a path of the X-ray radiated from the X-ray source 122 and adjusting an irradiation region radiated by the X-ray.

The X-ray source 122 includes an X-ray tube that may include a vacuum tube diode including a cathode and an anode. An inside of the X-ray tube is set as a high vacuum state of about 10 mmHg, and a filament of the anode is heated to a high temperature to generate thermal electrons. The filament may be a tungsten filament, and a voltage of about 10V and a current of about 3 to 5 A may be applied to an electric wire connected to the filament to heat the filament.

In addition, when a high voltage of about 10 to about 300 kVp is applied between the cathode and the anode, the thermal electrons are accelerated to collide with a target material of the cathode, and then, an X-ray is generated. The X-ray is radiated outside via a window, and the window may be formed of a beryllium thin film. In this case, most of the energy of the electrons colliding with the target material is consumed as heat, and remaining energy is converted into the X-ray.

The cathode is mainly formed of copper, and the target material is disposed opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, an energy of the X-ray (energy of photon) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The detector 130 detects an X-ray that is radiated from the X-ray emitter 120 and is transmitted through an object. The detector 130 may be a digital detector. The detector 130 may be implemented by using a thin-film transistor (TFT) or a charge-coupled device (CCD). Although the detector 130 is included in the X-ray apparatus 100 in FIG. 1, the detector 130 may be an X-ray detector that is a separate device capable of being connected to or separated from the X-ray apparatus 100.

The X-ray apparatus 100 may further include the manipulator 140 for providing a user with an interface for manipulating the X-ray apparatus 100. The manipulator 140 may include an output unit 141, e.g., an output transmitter such as a display device or a microphone, and an input unit 142, e.g., an input receiver. The input unit 142 may receive from a user a command for manipulating the X-ray apparatus 100 and various types of information related to X-ray imaging. The controller 150 may control or manipulate the X-ray apparatus 100 according to the information received by the input unit 142. The output unit 141 may output sound representing information related to a photographing operation such as the X-ray radiation under the control of the controller 150.

The workstation 110 and the X-ray apparatus 100 may be connected to each other by wire or wirelessly. When they are connected to each other wirelessly, a device (not shown) for synchronizing clock signals with each other may be further included. The workstation 110 and the X-ray apparatus 100 may exist within physically separate spaces.

The workstation 110 may include an output unit 111, e.g., an output transmitter such as a display device or a microphone, an input unit 112, e.g., an input receiver, and a controller 113, e.g., a microprocessor. The output unit 111 and the input unit 112 provide the user with an interface for manipulating the workstation 110 and the X-ray apparatus 200. The controller 113 may control the workstation 110 and the X-ray apparatus 200.

The X-ray apparatus 100 may be controlled via the workstation 110 or may be controlled by the controller 150 included in the X-ray apparatus 100. Accordingly, the user may control the X-ray apparatus 100 via the workstation 110 or may control the X-ray apparatus 100 via the manipulator 140 and the controller 150 included in the X-ray apparatus 100. In other words, the user may remotely control the X-ray apparatus 100 via the workstation 110 or may directly control the X-ray apparatus 100.

Although the controller 113 of the workstation 110 is separate from the controller 150 of the X-ray apparatus 100 in FIG. 1, FIG. 1 is only an example. As another example, the controllers 113 and 150 may be integrated into a single controller, and the single controller may be included in only one among the workstation 110 and the X-ray apparatus 100. Hereinafter, the controllers 113 and 150 may denote the controller 113 of the workstation 110 and/or the controller 150 of the X-ray apparatus 100.

The output unit 111 and the input unit 112 of the workstation 110 may provide the user with an interface for manipulating the X-ray apparatus 100, and the output unit 141 and the input unit 142 of the X-ray apparatus 100 may also provide the user with an interface for manipulating the X-ray apparatus 100. Although the workstation 110 and the X-ray radiation apparatus 100 include the output units 111 and 141, respectively, and the input units 112 and 142, respectively, in FIG. 1, embodiments are not limited thereto. Only one among the workstation 110 and the X-ray apparatus 100 may include an output unit or an input unit.

Hereinafter, the input units 112 and 142 may denote the input unit 112 of the workstation 110 and/or the input unit 142 of the X-ray apparatus 100, and the output units 111 and 141 may denote the output unit 111 of the workstation 110 and/or the output unit 141 of the X-ray apparatus 100.

Examples of the input units 112 and 142 may include a keyboard, a mouse, a touch screen, a voice recognizer, a fingerprint recognizer, an iris recognizer, and other input devices which are known to one of skilled in the art. The user may input a command for radiating the X-ray via the input units 112 and 142, and the input units 112 and 142 may include a switch for inputting the command. The switch may be configured so that a radiation command for radiating the X-ray may be input only when the switch is pushed twice.

In other words, when the user pushes the switch, a prepare command for performing a pre-heating operation for X-ray radiation may be input through the switch, and then, when the user pushes the switch once more, the radiation command for performing substantial X-ray radiation may be input through the switch. When the user manipulates the switch as described above, the controllers 113 and 150 generate signals corresponding to the commands input through the switch manipulation, that is, a prepare signal, and transmit the generated signals to the high voltage generator 121 for generating a high voltage for generating the X-ray.

When the high voltage generator 121 receives the prepare signal from the controllers 113 and 150, the high voltage generator 121 starts a pre-heating operation, and when the pre-heating is finished, the high voltage generator 121 outputs a ready signal to the controllers 113 and 150. In addition, the detector 130 also needs to prepare to detect the X-ray, and thus the high voltage generator 121 performs the pre-heating operation and the controllers 113 and 150 transmit a prepare signal to the detector 130 so that the detector 130 may prepare to detect the X-ray transmitted through the object. The detector 130 prepares to detect the X-ray in response to the prepare signal, and when the preparing for the detection is finished, the detector 130 outputs a ready signal to the controllers 113 and 150.

When the pre-heating operation of the high voltage generator 121 is finished and the detector 130 is ready to detect the X-ray, the controllers 113 and 150 transmit a radiation signal to the high voltage generator 121, the high voltage generator 121 generates and applies the high voltage to the X-ray source 122, and the X-ray source 122 radiates the X-ray.

When the controllers 113 and 150 transmit the radiation signal to the high voltage generator 121, the controllers 113 and 150 may transmit a sound output signal to the output units 111 and 141 so that the output units 111 and 141 output a predetermined sound and the object may recognize the radiation of the X-ray. The output units 111 and 141 may also output a sound representing information related to photographing in addition to the X-ray radiation. In FIG. 1, the output unit 141 is included in the manipulator 140; however, embodiments are not limited thereto, and the output unit 141 or a portion of the output unit 141 may be located elsewhere. For example, the output unit 141 may be located on a wall of an examination room in which the X-ray imaging of the object is performed.

The controllers 113 and 150 control positions of the X-ray emitter 120 and the detector 130, imaging timing, and imaging conditions, according to imaging conditions set by the user.

In more detail, the controllers 113 and 150 control the high voltage generator 121 and the detector 130 according to the command input via the input units 112 and 142 so as to control radiation timing of the X-ray, an intensity of the X-ray, and a region radiated by the X-ray. In addition, the control units 113 and 150 adjust the position of the detector 130 according to a predetermined imaging condition, and controls operation timing of the detector 130.

Furthermore, the controllers 113 and 150 generate a medical image of the object by using image data received via the detector 130. In detail, the controllers 113 and 150 may receive the image data from the detector 130, and then, generate the medical image of the object by removing noise from the image data and adjusting a dynamic range and interleaving of the image data.

The output units 111 and 141 may output the medical image generated by the controllers 113 and 150. The output units 111 and 141 may output information for the user to manipulate the X-ray apparatus 100, for example, a user interface (UI), user information, or object information. Examples of the output units 111 and 141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a 3D display, a transparent display, and various other output devices.

The workstation 110 shown in FIG. 1 may further include a communicator (not shown) that may be connected to a server 11, a medical apparatus 12, and a portable terminal 13 via a network 15.

The communicator may be connected to the network 15 by wire or wirelessly to communicate with the server 11, the medical apparatus 164, or the portable terminal 166. The communicator may transmit or receive data related to diagnosis of the object via the network 15, and may also transmit or receive medical images captured by the medical apparatus 164, for example, a CT apparatus, an MRI apparatus, or an X-ray apparatus. Moreover, the communicator may receive a medical history or treatment schedule of the object (e.g., a patient) from the server 11 to diagnose a disease of the object. Also, the communicator may perform data communication with the portable terminal 13 such as a mobile phone, a personal digital assistant (PDA), or a laptop computer of a medical doctor or a client, as well as the server 11 or the medical apparatus 164 in a hospital.

The communicator may include one or more elements enabling communication with external apparatuses. For example, the communicator may include a local area communication module, a wired communication module, and a wireless communication module.

The local area communication module refers to a module for performing local area communication with an apparatus located within a predetermined distance. Examples of local area communication technology may include, but are not limited to, a wireless local area network (LAN), Wi-Fi, Bluetooth, ZigBee, Wi-Fi Direct (WFD), ultra wideband (UWD), infrared data association (IrDA), Bluetooth low energy (BLE), and near field communication (NFC).

The wired communication module refers to a module for communicating by using an electrical signal or an optical signal. Examples of wired communication technology may include wired communication techniques using a pair cable, a coaxial cable, and an optical fiber cable, and other wired communication techniques that are known to one skilled in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 shown in FIG. 1 may include a plurality of digital signal processors (DSPs), an ultra-small calculator, and a processing circuit for special purposes (for example, high speed analog/digital (A/D) conversion, high speed Fourier transformation, and an array process).

In addition, communication between the workstation 110 and the X-ray apparatus 100 may be performed using a high speed digital interface, such as low voltage differential signaling (LVDS), asynchronous serial communication, such as a universal asynchronous receiver transmitter (UART), a low latency network protocol, such as error synchronous serial communication or a controller area network (CAN), or any of various other communication methods that are known to one skilled in the art.

Figure 2:
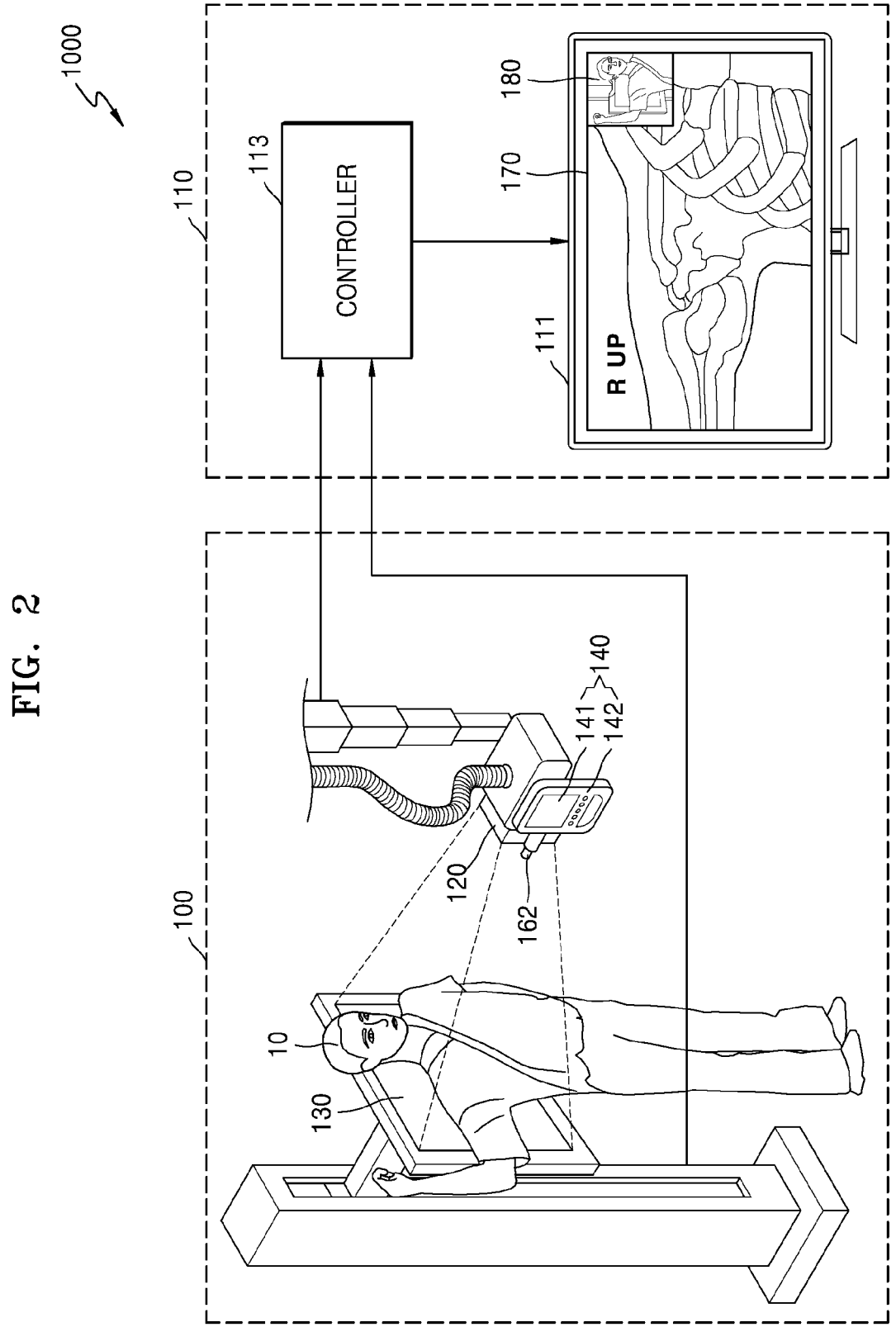
FIG. 2 is a conceptual view for explaining a method of generating an image marker according to an embodiment.

FIG. 2 is a conceptual view for explaining a method performed by the X-ray system 1000 to generate an image marker according to an embodiment.

Referring to FIG. 2, the X-ray system 1000 may include the X-ray apparatus 100 and the workstation 110. The X-ray apparatus 100 may include the X-ray emitter 120 that radiates X-rays to an object 10, the detector 130 that detects X-rays radiated from the X-ray emitter 120 and transmitted through the object 10, the manipulator 140 that provides a user interface (UI) for manipulating the X-ray apparatus 100, and an image obtainer 160 that is attached to a side of the X-ray emitter 120 and photographs the object 10.

The image obtainer 160 may obtain a plurality of still images of the object 10 by continuously photographing the object 10. The plurality of still images that are images obtained by the image obtainer 160 through photographing are different from an X-ray image that is obtained by x-ray imaging the object 10. The image obtainer 160 may be a camera that is a general apparatus for obtaining an image. The image obtainer 160 may include at least one of, for example, a complementary metal-oxide-semiconductor (CMOS) module, a CCD module, and an apparatus for taking a video. The image obtainer 160 may be attached to a side of the collimator 123 (see FIG. 1) of the X-ray emitter 120.

The workstation 110 may include the output unit 111 and the controller 113. The controller 113 may be connected to the X-ray apparatus 100 by wire or wirelessly. Although the controller 113 is included in the workstation 110 in FIG. 2, embodiments are not limited thereto. In an embodiment, the workstation 110 may be included in the X-ray apparatus 100.

The controller 113 may select a representative still image that represents a body part of the object 10 to be X-ray imaged (hereinafter, referred to as a to-be-X-ray imaged or candidate body part of the object 10) among the plurality of still images obtained by the image obtainer 160 by continuously photographing the object 10, and may generate the image marker 180 by performing image processing on the selected representative still image. The X-ray apparatus 100 may detect X-rays radiated to the object 10 from the X-ray emitter 120 and transmitted through the object 10 by using the detector 130, and the controller 113 of the workstation 110 may receive image data through the detector 130 and may obtain an X-ray image 170 of the object 10 by performing image processing on the received image data. In an embodiment, the controller 113 may display the image marker 180 so that the image marker 180 overlaps a first region of the X-ray image 170.

The output unit 111 of the workstation 110 may display the image marker 180 along with the X-ray image 170 by causing the image marker 180 to overlap the X-ray image 170. In an embodiment, the X-ray image 170 and the image marker 180 may also be displayed on the manipulator 140 of the X-ray apparatus 100.

In general, the X-ray imaging is performed by imaging various body parts of the object 10 in a given imaging direction for diagnostic purposes. In this case, examples of the imaging direction may include an antero-posterior (AP) direction in which the object 10 is imaged from front to back, a postero-anterior (PA) direction in which the object is imaged from back to front, a lateral right/left (R/L) direction in which the object 10 is laterally imaged, and an oblique R/L direction in which the object 10 is obliquely imaged. The X-ray image 170 captured by a user of the X-ray system 1000, for example, a radiologist, may be oriented or flipped before being transmitted to an examining doctor. In this case, a marker that may be observed by the examining doctor is needed. However, when a marker that is preset in the X-ray system 1000 is different from an actual imaging condition or the radiologist makes a mistake, a wrong marker may be used, thereby leading to a medical mistake or malpractice.

The X-ray system 1000 according to an embodiment may generate a still image, obtained by the image obtainer 160 by photographing the object 10, as the image marker 180 and may display the image marker 180 so that the image marker 180 overlaps the X-ray image 170. Since the X-ray system 1000 according to an embodiment photographs an appearance of the object 10 at a photographing time and directly uses a still image of the object 10 as an image marker, the user (e.g., a radiologist or an examining doctor) may easily recognize and determine whether the X-ray image 170 has been captured in a normal imaging direction, has been flipped, or in particular, has been vertically or horizontally flipped. Accordingly, a medical malpractice which occurs when the user, in particular, the examining doctor, fails to detect whether the X-ray image 170 is vertically or horizontally flipped and mistakenly diagnoses a disease of the object 10, may be prevented in advance.

Figure 3:
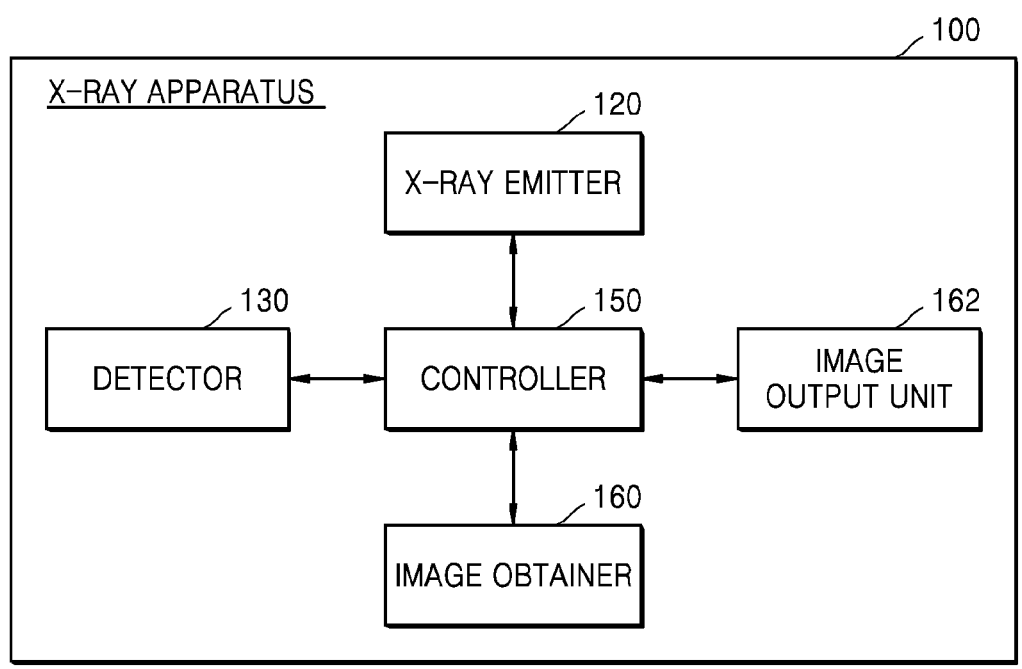
FIG. 3 is a block diagram of an X-ray apparatus according to an embodiment.

FIG. 3 is a block diagram of the X-ray apparatus 100 according to an embodiment.

Referring to FIG. 3, the X-ray apparatus 100 may include the X-ray emitter 120, the detector 130, the controller 150, the image obtainer 160, and an image output unit 162. The X-ray emitter 120 and the detector 130 are the same as those in FIGS. 1 and 2, and thus a repeated explanation thereof will not be provided.

The image obtainer 160 may include a camera attached to a side of the X-ray emitter 120 (see FIG. 2). The camera may be disposed to face the object 10 (see FIG. 2) and may include a camera sensor configured to convert an image of the object 10 into an electrical signal and a signal processor configured to convert an analog image signal transmitted from the camera sensor into digital data. The camera sensor may be a CCD or CMOS sensor, and the signal processor may be a DSP. The camera sensor may photograph the object 10 and the signal processor may obtain a captured image of the object 10. In an embodiment, the camera sensor may continuously photograph the object 10 and the signal processor may obtain a plurality of still images of the object 10.

The controller 150 may select one from the plurality of still images of the object 10 obtained by the image obtainer 160 and may generate the selected still image as a representative still image. The representative still image may be a still image that represents a candidate body part of the object 10.

The controller 150 may generate the image marker 180 (see FIG. 2) by performing image processing on a captured image of the object 10. In an embodiment, the controller 150 may perform image processing on the representative still image selected from the plurality of still images obtained by the image obtainer 160 by photographing the object 10 and may generate the image-processed representative still image as the image marker 180. In an embodiment, the controller 150 may generate the representative still image itself as the image marker 180. However, embodiments are not limited thereto, and the controller 150 may generate the image marker 180 by using image processing that blurs and/or mosaics the representative still image. Also, the controller 150 may generate the X-ray image 170 (see FIG. 2) of the object 10 and may cause the image marker 180 to overlap the generated X-ray image 170. In an embodiment, the controller 150 may cause the image marker 180 to overlap a first region in the X-ray image 170 by reducing a size of the image marker 180 to be less than that of the X-ray image 170.

The controller 150 may include a hardware element such as a field-programmable gate array (FPGA) or an application-specific integrated circuit (ASIC). For example, the controller 150 may be a hardware device including at least one among hardware units including a central processing unit (CPU), a microprocessor, a graphics processing unit (GPU), and a memory The controller 150 may control the X-ray image 170 and the image marker 180 to be displayed on the image output unit 162. In an embodiment, the controller 150 may store the image marker 180 in a digital imaging and communications in medicine (DICOM) header, instead of simultaneously displaying the image marker 180 and the X-ray image 170. Once the image marker 180 is stored in the DICOM header, the controller 150 may determine whether to display the image marker 180 according to option settings of the user.

The image output unit 162 may display the X-ray image 170 which the image marker 180 overlaps to the user. The image marker 180 may be displayed so that the image marker 180 overlaps the first region of the X-ray image 170.

In an embodiment, the image output unit 162 may display a UI for manipulating the X-ray apparatus 100 by using the X-ray image 17 and the image marker 180. When the image output unit 162 displays the X-ray image 170, the image marker 180, and the UI, the image output unit 162 may be a touch screen for receiving a touch input of the user.

Figure 4:
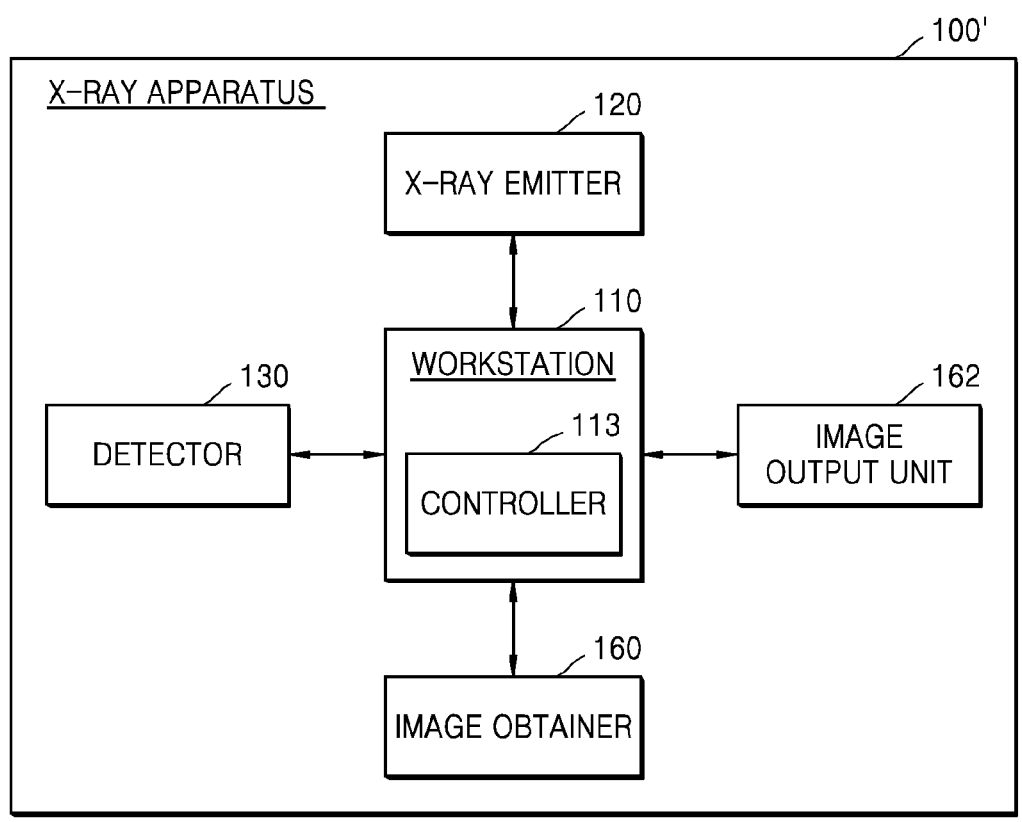
FIG. 4 is a block diagram of an X-ray apparatus according to an embodiment.

FIG. 4 is a block diagram of an X-ray apparatus 100' according to an embodiment.

Referring to FIG. 4, the X-ray apparatus 100' may include the workstation 110, the X-ray emitter 120, the detector 130, the image obtainer 160, and the image output unit 162. The X-ray emitter 120, the detector 130, the image obtainer 160, and the image output unit 162 of FIG. 4 are the same as those in FIG. 3, and thus a repeated explanation thereof will not be provided.

The workstation 110 may include the controller 113. The controller 113 may generate the image marker 180 (see FIG. 2) by performing image processing on a captured image of the object 10 obtained by the image obtainer 160. Also, the controller 113 may generate the X-ray image 170 (see FIG. 2) of the object 10 based on X-rays detected by the detector 130, and may cause the image marker 180 to overlap the generated X-ray image 170.

In any embodiment of the specification, the controller 113 may perform the same function and operation as that of the controller 150 of FIG. 3, and thus a repeated explanation thereof will not be provided.

Figure 5:
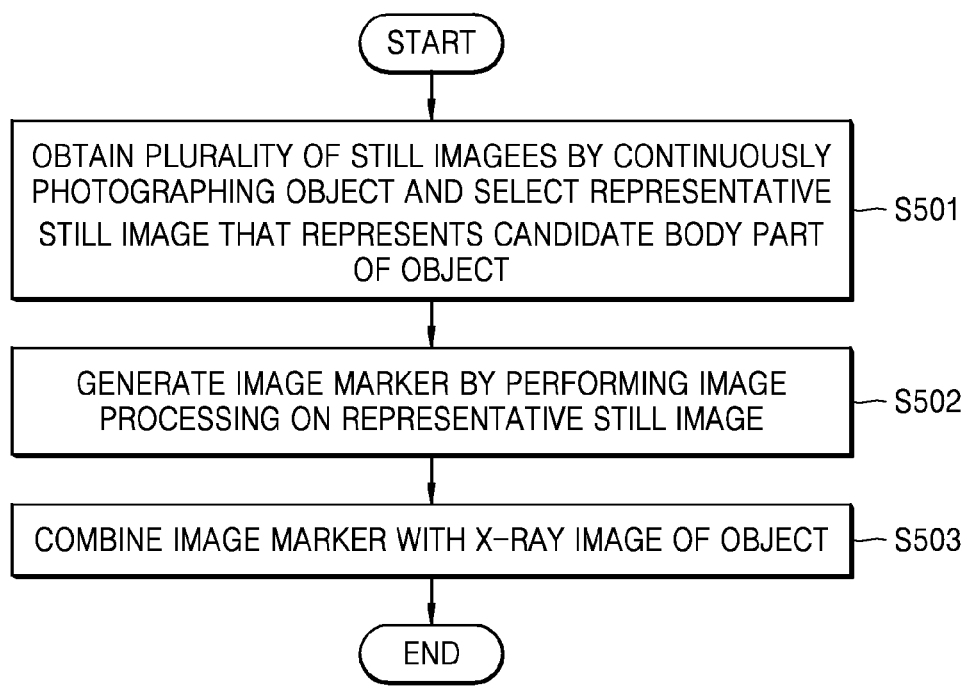
FIG. 5 is a flowchart of a method performed by the X-ray apparatus to generate an image marker according to an embodiment.

FIG. 5 is a flowchart of a method performed by the X-ray apparatus of FIG. 3 to generate the image marker 180.

In operation S501, the X-ray apparatus obtains a captured image of an object by continuously photographing the object and selects a representative still image that represents a candidate body part of the object. In an embodiment, the X-ray apparatus may obtain a plurality of still images of the object by continuously photographing the object. The captured image of the object may be different from an X-ray image obtained by X-ray imaging the object. The plurality of still images may be obtained by a camera for obtaining an image. In an embodiment, the image obtainer 160 (see FIG. and 3) may obtain a plurality of still images of the object 10 (see FIG. 2) by continuously photographing the object 10.

The X-ray apparatus may select a representative still image that represents a candidate body part of the object from among the plurality of still images. In an embodiment, the X-ray apparatus may recognize an image that is clearly captured because a camera is accurately focused on the candidate body part of the object by performing image processing on all of the plurality of still images and may determine the recognized image as a representative still image.

In operation S502, the X-ray apparatus generates an image marker by performing image processing on the captured image. In an embodiment, the image marker may be generated by using image processing that blurs or mosaics the captured image. In an embodiment, a shape of the object included in the captured image is recognized by performing image processing on the captured image, and the image marker may be a cartoon image similar to the recognized shape. However, embodiments are not limited thereto, and the image marker may be the captured image itself, or may include the same image as the captured image. In an embodiment, the controller 150 or 113 (see FIG. 3) may generate the image marker by performing image processing on a representative still image among the plurality of still images of the object.

In operation S503, the X-ray apparatus combines the image marker with an X-ray image of the object. In an embodiment, a size of the image marker may be less than a size of the X-ray image. In an embodiment, the controller 150 or 113 (see FIG. 3) may combine the image marker with the X-ray image so that the image marker overlaps a first region in the X-ray image.

Figure 6A:
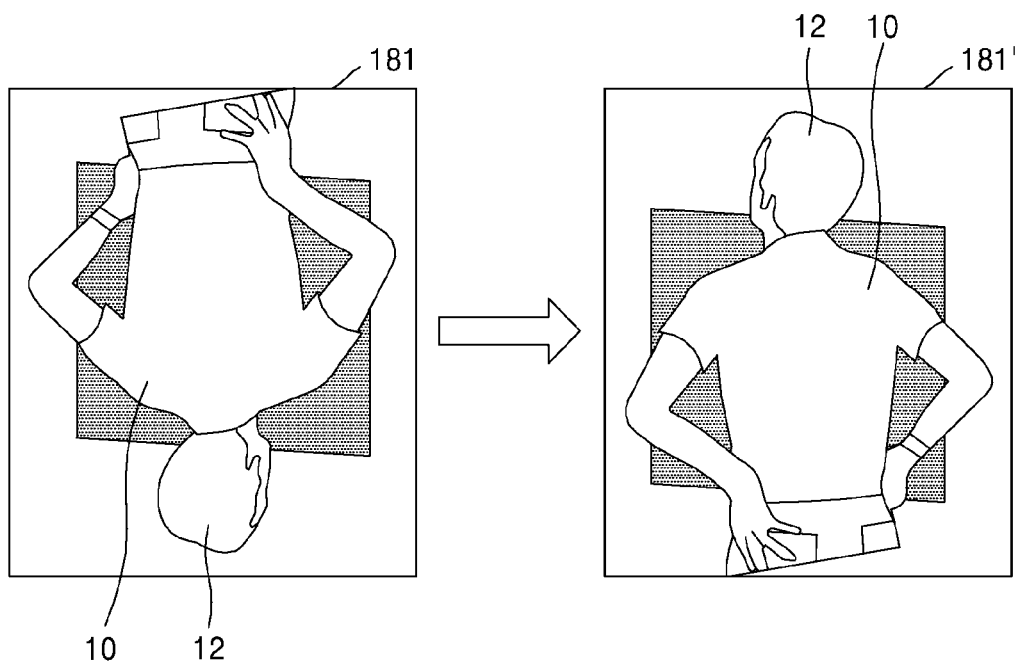
FIGS. 6A, 6B, and 6C are views for explaining a method of correcting a captured image according to an embodiment.
Figure 6B:
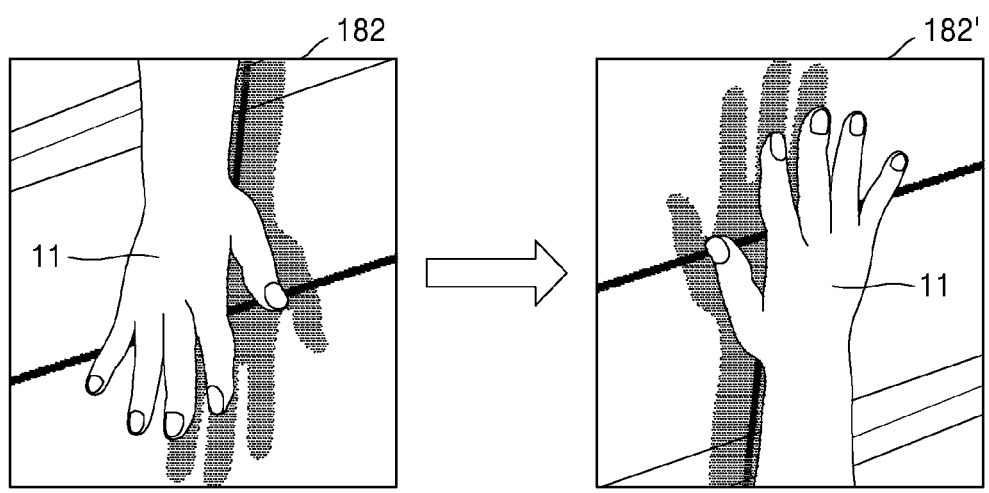
Figure 6C:
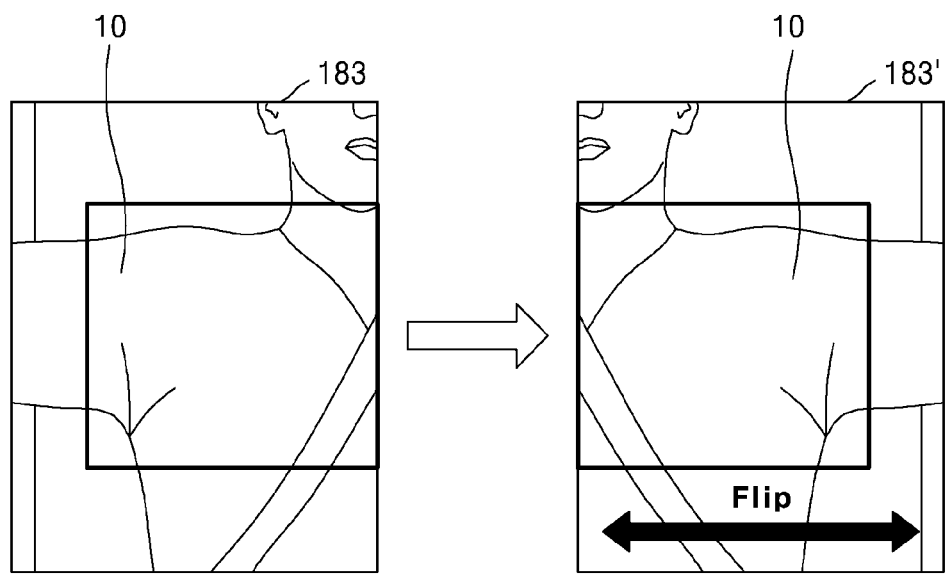

FIGS. 6A through 6C are views for explaining a method of correcting a still image of an object according to an embodiment.

Referring to FIG. 6A, a first representative still image 181 is vertically flipped to generate a first corrected image 181'. The first corrected image 181' may be an image in which the object 10 included in the first representative still image 181 is vertically flipped. In an embodiment of FIG. 6A, a target body part of the object 10 may be the chest of a patient, and the first representative still image 181 may be an image with the head 12 of the object 10 upside down. In an embodiment, the controller 150 (see FIG. 3) may recognize the head 12 of the patient included in the first representative still image 181 and may vertically flip the first representative still image 181 so that the head 12 of the patient is on an upper side. Since the first corrected image 181' is generated by correcting the head 12 of the patient included in the first representative still image 181 to be on the upper side, a user may intuitively recognize a direction of the patient, that is, the object 10.

Referring to FIG. 6B, a second representative still image 182 may be vertically flipped, like the first representative still image 181. In an embodiment of FIG. 6B, a target body part of an object 11 may be the hand of a patient, and the second representative still image 182 may be vertically flipped so that fingers are on an upper side to obtain a second corrected image 182'. In an embodiment, when the object 11 included in the second representative still image 182 is not located at a central portion of the second representative still image 182, the second corrected image 182' may be generated by correcting a position of the object 11. The controller 150 (see FIG. 3) may generate the second corrected image 182' by correcting a direction and/or a position of the second representative still image 182.

Referring to FIG. 6C, a third representative still image 183 may be horizontally flipped to generate a third corrected image 183'. The third corrected image 183' may be an image in which the object 10 included in the third representative still image 183 is horizontally flipped. In an embodiment of FIG. 6C, although a target body part of the object 10 includes the right side of the chest and the right shoulder of the patient and the right side of the chest and the right shoulder of the object 10 were actually X-ray imaged, if a user (e.g., an examining doctor) recognizes as if the left side of the chest and the left shoulder are X-ray imaged, the third corrected image 183' may be generated by flipping the third representative still image 183 for better intuitive understanding of the user. In an embodiment, a symbol such as a left right arrow indicating a horizontal flip may be displayed on the third corrected image 183'. Also, a text or a word, e.g., a word "Flip" indicating that an image is horizontally flipped may be displayed on the third corrected image 183'. However, embodiments are not limited thereto, and although not shown in FIG. 6C, the third corrected image 183' may include a text or a word, e.g., a letter "R" to indicate that an image is obtained by photographing the right side of the chest and the right shoulder of the object 10.

Referring back to FIG. 3, the controller 150 (see FIG. 3), the image obtainer 160 (see FIG. 3) may select a representative still image that represents a candidate body part of an object among a plurality of still images of the object obtained by the image obtainer 160 (see FIG. 3) by continuously photographing the object. The controller 150 may select a still image that is obtained immediately before X-ray imaging among the plurality of still images as a representative still image. In an embodiment, the controller 150 may recognize an image that is clearly captured because a camera is accurately focused on the candidate body part of the object by performing image processing on all of the plurality of still images, and may determine the recognized image as a representative still image. In an embodiment, the controller 150 may recognize an image whose candidate body part of the object is the brightest by performing image processing on all of the plurality of still images, and may determine the recognized image as a representative still image.

The controller 150 may also correct a direction and/or a position of the representative still image. In an embodiment, the controller 150 may recognize the object included in the representative still image by performing image processing on the representative still image and may recognize direction information and/or position information of the object. The controller 150 may also correct the representative still image based on the recognized direction information and/or the recognized position information. In an embodiment, the controller 150 may perform pre-processing by adjusting a brightness or a dynamic range of the representative still image. In an embodiment, the controller 150 may correct a direction and/or a position of the representative still image by using direction and position information preset in the X-ray apparatus 100 or the workstation 110. However, embodiments are not limited thereto, and the controller 150 may correct a direction and/or a position of the representative still image by using geometric information of a system and an image processing algorithm.

The controller 150 may generate an image marker by performing image processing on the representative still image. The controller 150 may blur or mosaic the representative still image and may generate the blurred or mosaic-processed representative still image as an image maker. The controller 150 may recognize an outline or a shape of the object included in the representative still image by performing image processing on the representative still image and may generate a cartoon image having the recognized outline or the recognized shape as an image marker.

FIGS. 7A through 7D are views for explaining an image processing method of generating an image marker by using a representative still image according to an embodiment.

Figure 7A:
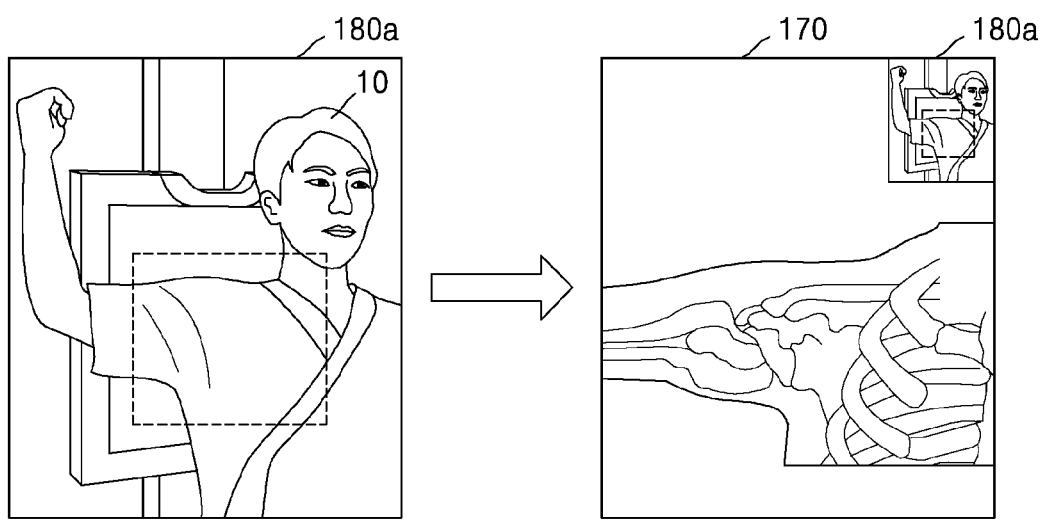

Referring to FIG. 7A, a representative still image itself may be an image marker 180a without performing additional image processing on the representative still image. The image maker 180a may overlap a first region of the X-ray image 170. In an embodiment of FIG. 7A, since the representative still image that is obtained by photographing a patient whose right side of the chest and right shoulder are being X-ray imaged is the image marker 180a, a user (in this case, an examining doctor) may intuitively know how which body part of the patient has been X-ray imaged when interpreting an X-ray image.

Figure 7B:
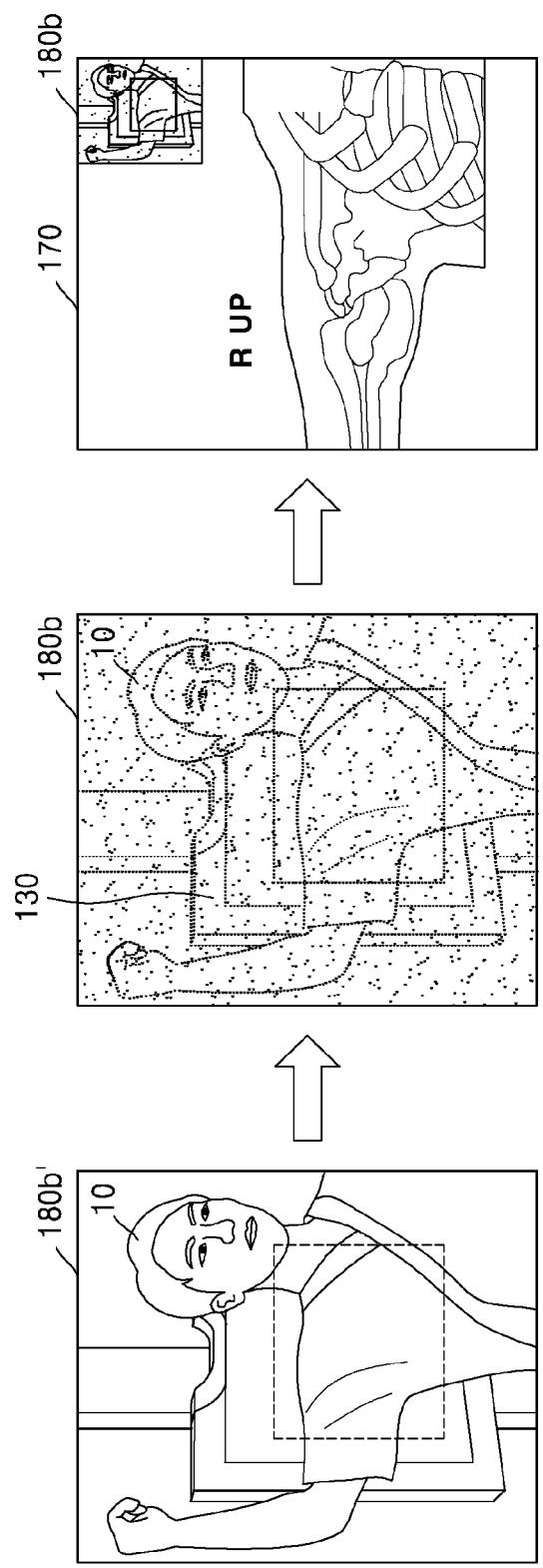

Referring to FIG. 7B, a representative still image 180b' may be blurred and may be generated as an image marker 180b. An outline and a shape of the object 10 included in the representative still image 180b' may be blurred so that only minimum information such as a position of the object 10 on the detector 130 or a candidate body part may be recognized. The image maker 180b that is blurred may overlap the first region of the X-ray image 170 and may be displayed along with the X-ray image 170.

Figure 7C:
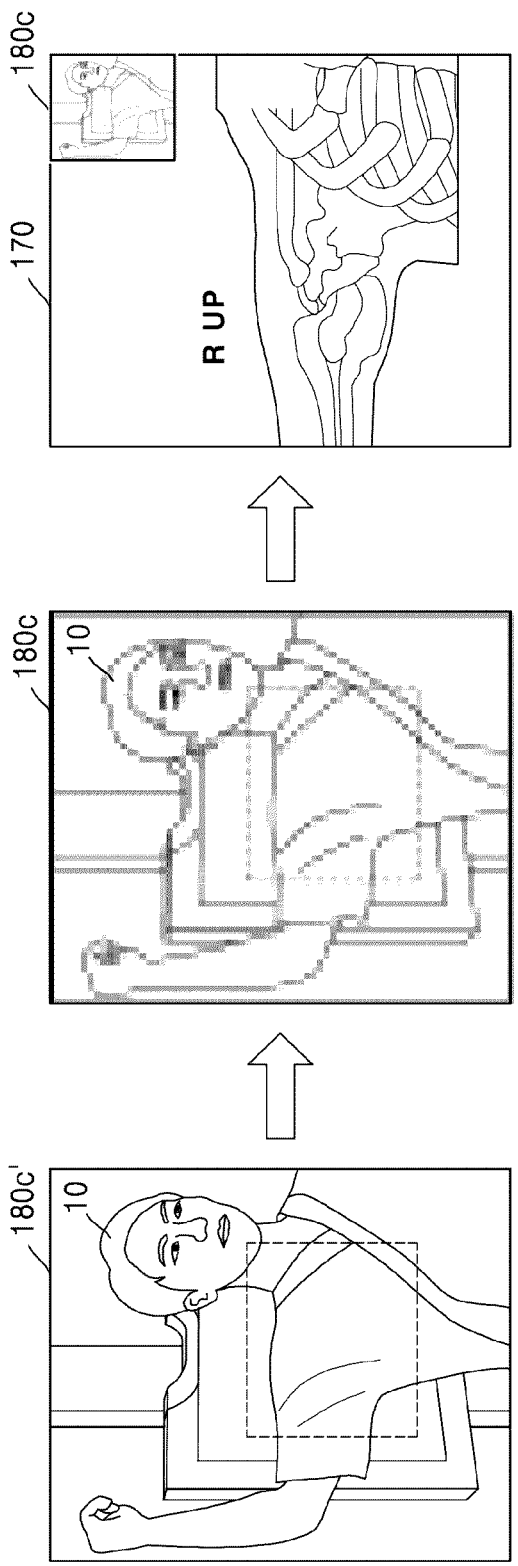

Referring to FIG. 7C, a representative still image 180c' may be mosaic-processed and may be generated as an image maker 180c. Like in FIG. 7B, an outline and a shape of the object 10 included in the representative still image 180c' may be mosaic-processed so that only a candidate body part of the object 10 and a position of the candidate body part are recognized. The image marker 180c that is mosaic-processed may overlap the first region of the X-ray image 170 and may be displayed along with the X-ray image 170.

In an embodiment of FIG. 7B or 7C, the representative still image 180b' or 180c' is blurred or mosaic-processed so that a user (e.g., a radiologist or an examining doctor) does not recognize a captured image of the object 10, that is, a patient, included in the representative still image 180b' or 180c'. This is to prevent the risk of the patient's privacy invasion. In detail, when the patient does not want to expose body parts other than a candidate body part or the patient's body secret may be possibly exposed, a captured image of the patient including the candidate body part may be blurred or mosaic-processed, to prevent the risk of privacy invasion.

Referring to FIG. 7D, a representative still image 180d' may be replaced with a cartoon image and the cartoon image may be an image marker 180*d*. In an embodiment, a cartoon image may be generated by performing image processing that simply illustrates an outline and a shape of the object 10, included in the representative still image 180*d'*, with only lines and surface and may be the image marker 180*d*. In an embodiment, an outline and a shape of the object 10 included in the representative still image 180*d* may be recognized by performing image processing on the representative still image 180*d'*, the recognized outline and the recognized shape of the object 10 may be compared with images pre-stored in a storage such as a database to select a most similar cartoon image, the most similar cartoon image may be the image marker 180*d*, and the image marker 180*d* may overlap the X-ray image 170. In an embodiment of FIG. 7D, since a captured image of the object 10, that is, a patient, included in the representative still image 180*d'*, is changed into a cartoon image by performing image processing on the captured image, the risk of the patient's privacy invasion may be prevented, like in FIGS. 7B and 7C.

Figure 8:
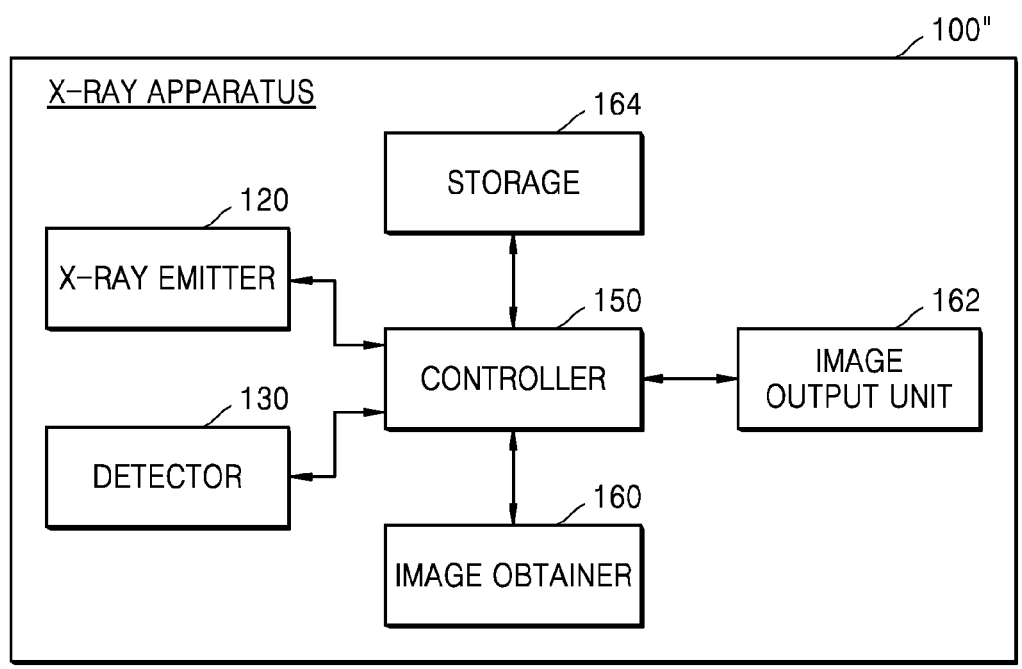
FIG. 8 is a block diagram of an X-ray apparatus according to an embodiment.

FIG. 8 is a block diagram of an X-ray apparatus 100" according to an embodiment. Referring to FIG. 8, the X-ray apparatus 100" may include the X-ray emitter 120, the detector 130, the controller 150, the image obtainer 160, the image output unit 162, and a storage 164. The X-ray emitter 120, the detector 130, the image obtainer 160, and the image output unit 162 are the same as those in FIG. 3, and thus a repeated explanation thereof will not be provided.

The controller 150 may select a representative still image among a plurality of still images obtained by the image obtainer 160 by continuously photographing an object, and may generate an image marker by performing image processing such as blurring, mosaic processing, and cartoon imaging on the representative still image. In an embodiment, the controller 150 may generate the representative still image itself as an image marker without performing additional image processing on the representative still image. The reason why the controller 150 performs image processing on the representative still image so that a user (e.g., a radiologist or an examining doctor) might not recognize an outline or a shape of the object is that the risk of a patient's privacy invasion is prevented as described with reference to FIGS. 7B through 7D. In an embodiment, the controller 150 may select any one among blurring, mosaic processing, and cartoon imaging as image processing according to option settings of the X-ray apparatus 100".

The storage 164 may store cartoon images or object sample images that may replace the representative still image. In an embodiment, the storage 164 may include at least one among a volatile memory (e.g., a dynamic random-access memory (DRAM), a static RAM (SRAM), or a synchronous dynamic RAM (SDRAM)), a nonvolatile memory (e.g., a one-time programmable ROM (OTPROM), a programmable ROM (PROM), an erasable and programmable ROM (EPROM), an electrically erasable and programmable ROM (EEPROM), a mask ROM, or a flash ROM), a hard disk drive (HDD), and a solid-state drive (SSD). In an embodiment, the storage 164 may include a database.

The controller 150 may recognize an outline and a shape of the object included in the representative still image by performing image processing on the representative still image, and may compare the recognized outline and the recognized shape of the object with the cartoon images or the object sample images stored in the storage 164. The controller 150 may select an image that is most similar to the object included in the representative still image among the cartoon images or the object sample images stored in the storage 164 and may generate an image marker by using the selected image. In an embodiment, the controller 150 may cause the generated image marker to overlap an X-ray image and may display the image marker along with the X-ray image.

Figure 9:
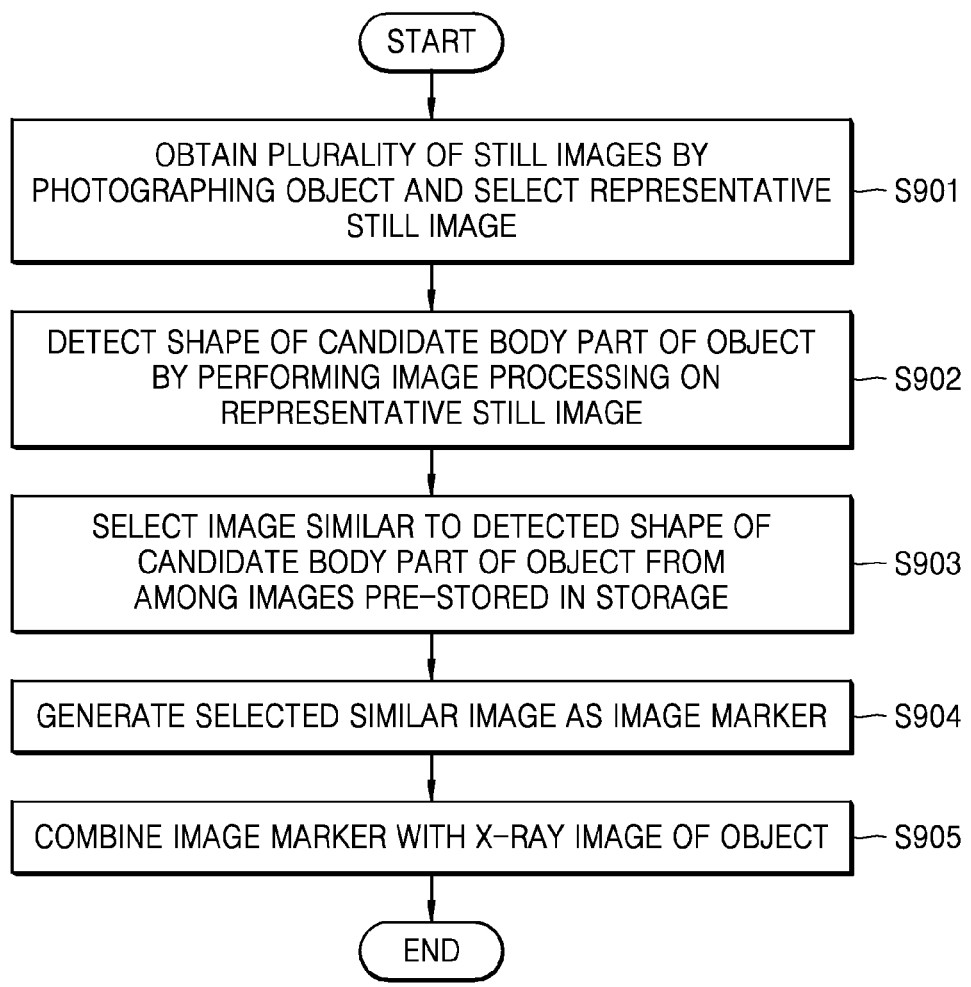
FIG. 9 is a flowchart of a method performed by the X-ray apparatus of FIG. 8 to generate an image marker.

FIG. 9 is a flowchart of a method performed by the X-ray apparatus 100" of FIG. 8 to generate an image marker.

In operation S901, an X-ray apparatus obtains a plurality of still images by continuously photographing an object, and selects a representative still image that represents a candidate body part of the object among the plurality of still images. The representative still image may be a still image obtained by photographing the candidate body part of the object among still images obtained immediately before X-ray imaging among the plurality of still images. The obtaining of the plurality of still images and the selecting of the representative still image are the same as those described in operation S501 of FIG. 5, and thus a repeated explanation thereof will not be provided.

In operation S902, a shape of the candidate body part of the object is recognized by performing image processing on the representative still image. The X-ray apparatus may recognize an outline and a shape of the object included in the representative still image by performing image processing on the representative still image. In an embodiment, the controller 150 (see FIG. 8) may recognize the object included in the representative still image by using one of image recognition techniques known in the art.

In operation S903, an image that is similar to the recognized shape of the candidate body part of the object is selected among images pre-stored in a storage. In an embodiment, the controller 150 (see FIG. 8) may recognize an outline and a shape of the candidate body part of the object included in the representative still image by using image recognition, and may compare the recognized outline and the recognized shape of the object with images pre-stored in the storage 164 (see FIG. 8). Also, the controller 150 may compare the recognized outline and the recognized shape of the object with cartoon images and/or object sample images stored in the storage 164, and may select an image that is most similar to the recognized outline and the recognized shape of the object among the cartoon images and/or the object sample images. The storage 164 may be a memory included in the workstation 110. However, embodiments are not limited thereto, and the storage 164 may be an external database.

In operation S904, the selected similar image is generated as an image marker. In an embodiment, the controller 150 (see FIG. 8) may generate an image marker by using a cartoon image or an object sample image selected in operation S903.

Figure 10:
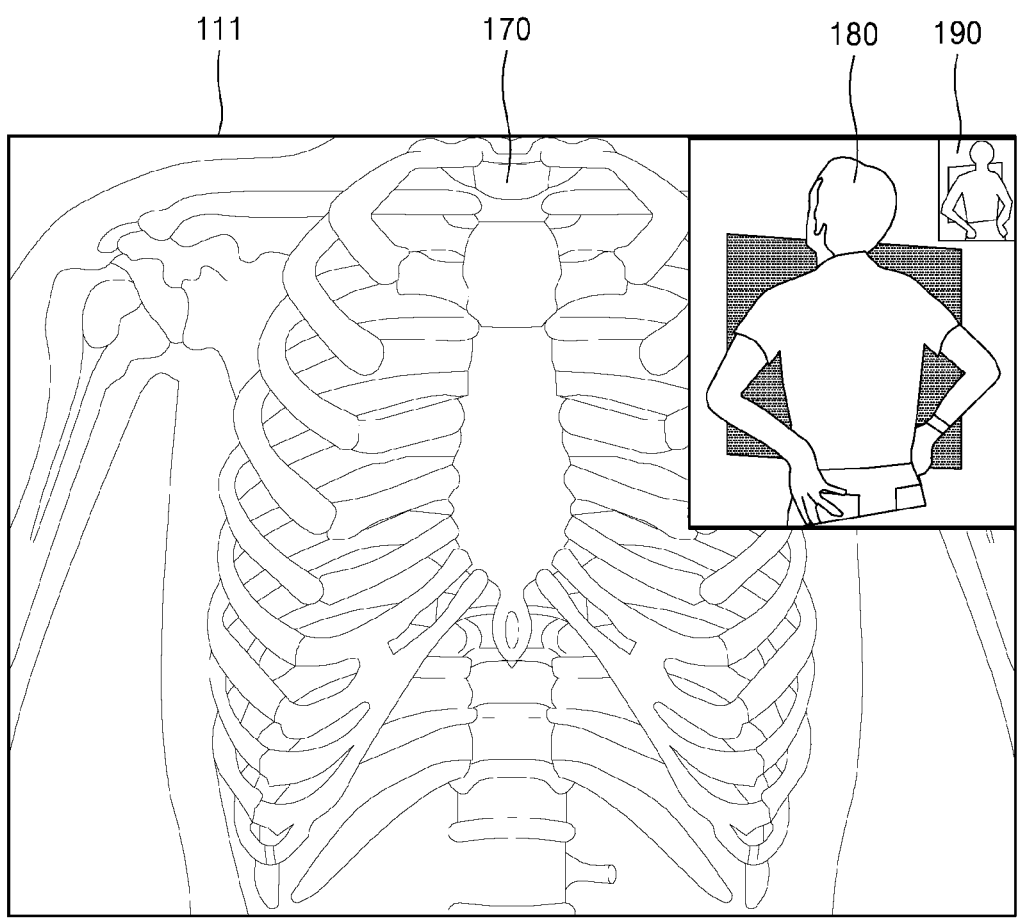
FIG. 10 shows an X-ray image including an image marker and a guide image according to an embodiment.

In operation S905, the image marker is combined with an X-ray image. The image marker combined with the X-ray image may overlap the X-ray image and may be output together with the X-ray image on the image output unit 162 (see FIG. 8) or the output unit 111 (see FIG. 2) of the workstation 110. However, embodiments are not limited thereto, and the image marker may be stored in a DICOM header, instead of or in addition to being displayed on the image output unit 162 or the output unit 111 based on display option settings of a user. FIG. 10 shows the X-ray image 170 including the image marker 180 and a guide image 190 according to an embodiment.

Referring to FIG. 10, the image marker 180 may be formed on a region of the X-ray image 170, and the guide image 190 may be included in the image marker 180. The guide image 190 may be an image that enables a user to recognize a vertical/horizontal direction of the image marker 180. In an embodiment, the guide image 190 may be a figure image or a cartoon image including text and/or an arrow.

In an embodiment of FIG. 10, the guide image 190 may be a cartoon image. Since the guide image 190 is displayed along with the image marker 180 on a region of the image marker 180, the user (e.g., an examining doctor) may easily recognize in what shape the object 10 is X-ray imaged by using the left and right sides of the image marker 180. In an embodiment, the guide image 190 may be displayed as at least one among an arrow, a figure, and a word, e.g., a word "Flip," indicating that the X-ray image 170 is horizontally flipped on the image marker 180.

Referring back to FIG. 3, the controller 150 (see FIG. 3) may select a representative still image that represents a candidate body part among a plurality of still images of an object obtained by the image obtainer 160 by continuously photographing the object, and may generate an image marker by performing image processing on the selected representative still image. In an embodiment, the controller 150 may blur or mosaic the representative still image, and may generate the blurred or mosaic-processed representative still image as an image marker.

The controller 150 may generate a guide image that enables a user to recognize an X-ray imaging direction of the object included in the image marker. In an embodiment, the guide image may be at least one among a text, an arrow, and a figure image that enables the user to recognize a vertical or horizontal direction of the image marker. In an embodiment, the controller 150 may perform image processing on the image marker to generate a cartoon image, and may generate a guide image by using the cartoon image. The controller 150 may generate a cartoon image by using image recognition that recognizes an outline and a shape of an image of the object included in the image marker. However, embodiments are not limited thereto, and the controller 150 may generate a guide image including an arrow or a text, e.g., a word "Flip," that enables the user to recognize whether the image marker is horizontally flipped.

Figure 11:
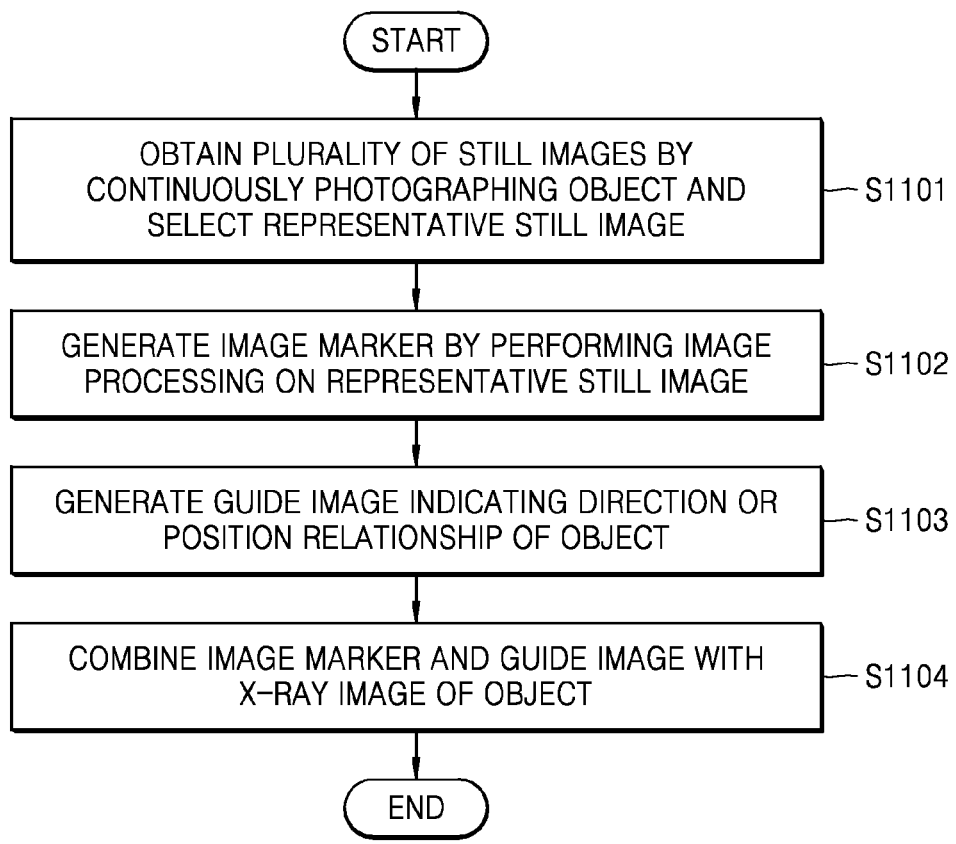
FIG. 11 is a flowchart of a method performed by the X-ray apparatus to generate an image marker including a guide image according to an embodiment.

FIG. 11 is a flowchart of a method performed by the X-ray apparatus 100 of FIG. 3 to generate an image marker including a guide image.

In operation S1101, an X-ray apparatus obtains a plurality of still images by continuously photographing an object, and selects a representative still image among the obtained plurality of still images of the object. The obtaining of the plurality of still images and the selecting of the representative still image are the same as those described in operation S501 of FIG. 5, and thus a repeated explanation thereof will not be provided.

In operation S1102, an image marker is generated by performing image processing on the representative still image. In an embodiment, the image marker may be an image obtained by blurring or mosaic processing the representative still image. The generating of the image marker is the same as that described in operation S502 of FIG. 5, and thus a repeated explanation thereof will not be provided.

In operation S1103, the X-ray apparatus generates a guide image indicating a direction or position relationship of the object. In an embodiment, the controller 150 included in the workstation 110 may perform image processing on the image marker generated in operation S1102 to obtain a cartoon image, and may generate a guide image by using the cartoon image. However, the guide image is not limited to a cartoon image, and may be at least one among a text, an arrow, and a figure image that enables a user to recognize a vertical/horizontal direction of the image marker.

Figure 12:
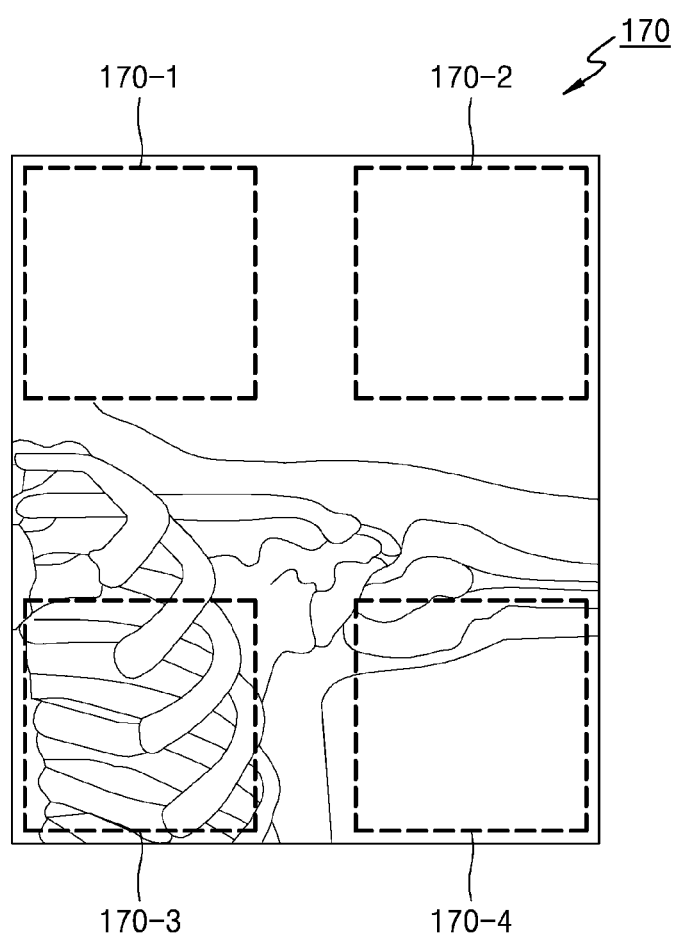
FIG. 12 is a view for explaining a method of determining a position of an image marker according to an embodiment.

In operation S1104, the X-ray apparatus combines the image marker and the guide image with an X-ray image of the object. The guide image may be combined to overlap a region of the image marker. The image marker combined with the guide image may overlap a region of the X-ray image obtained by X-ray imaging the object and may be simultaneously displayed along with the X-ray image. FIG. 12 is a view for explaining a method of determining a position of an image marker according to an embodiment.

Referring to FIG. 12, the X-ray image 170 obtained by X-ray imaging an object may include a first region 170-1 through a fourth region 170-4. In an embodiment of FIG. 12, a target body part of the object may be the right side of the chest and the right shoulder of a patient. Although the X-ray image of the object is divided into the first region 170-1 through the fourth region 170-4 according to regions in FIG. 12, embodiments are not limited thereto. Alternatively, the X-ray image 170 may be divided into less or more regions, instead of four regions.

In an embodiment, the first region 170-1 and the second region 170-2 may include clinical information about the object that is less than that of the third region 170-3 and the fourth region 170-4. An image marker may overlap the first region 170-1 or the second region 170-2 including relatively minor clinical information of the object. Accordingly, when the image marker overlaps the X-ray image 170 and is simultaneously displayed along with the X-ray image 170, a user may obtain sufficient clinical information of the object displayed on the X-ray image 170. However, embodiments are not limited thereto, and the image marker may automatically overlap a region preset in an X-ray apparatus and may be displayed.

Referring back to FIG. 3, the controller 150 (see FIG. 3) may select a representative still image that represents a candidate body part among a plurality of still images of an object obtained by the image obtainer 160 by continuously photographing the object, and may generate an image marker by performing image processing on the selected representative still image. The controller 150 may determine a region which the image marker overlaps in an X-ray image. In an embodiment, the controller 150 may determine a position of the image marker that overlaps in the X-ray image based on preset information according to an imaging protocol or the candidate body part of the object.

Figure 13:
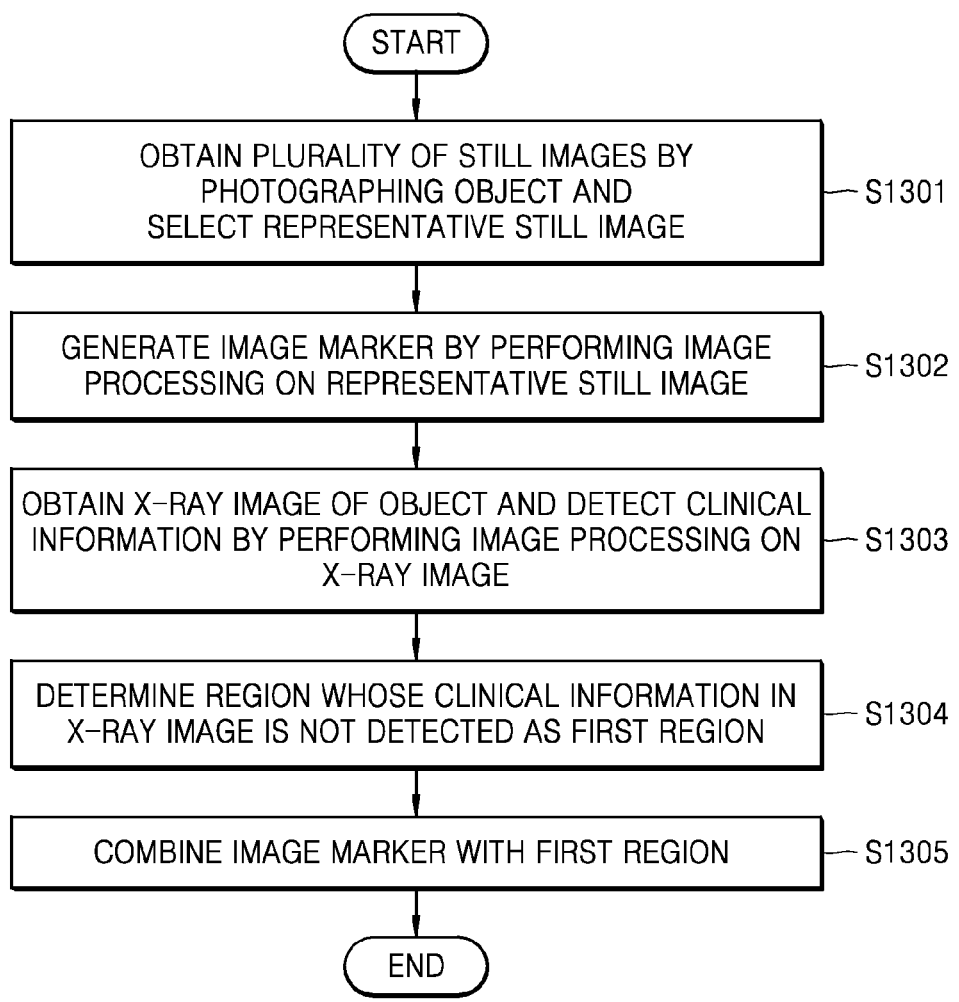
FIG. 13 is a flowchart of a method performed by the X-ray apparatus to determine a position of an image marker according to an embodiment.

In an embodiment, the controller 150 may detect a region including relatively minor clinical information of the object in the X-ray image by performing image processing on the X-ray image obtained by X-ray imaging the object, and may cause the image marker to overlap the detected region. For example, the controller 150 may determine a position of the image marker so that the image marker overlaps a background portion or a corner portion of the X-ray image that has insubstantial clinical information. FIG. 13 is a flowchart of a method performed by the X-ray apparatus 100 of FIG. 3 to determine a position of an image marker.

In operation S1301, an X-ray apparatus obtains a plurality of still images by continuously photographing an object and selects a representative still image. The obtaining of the plurality of still images and the selecting of the representative still image are the same as those described in operation S501 of FIG. 5, and thus a repeated explanation thereof will not be provided.

In operation S1302, an image marker is generated by performing image processing on the representative still image. In an embodiment, the image marker may be obtained by blurring or mosaic processing the representative still image. The generating of the image marker is the same as that described in operation S502 of FIG. 5, and thus a repeated explanation thereof will not be provided.

In operation S1303, the X-ray apparatus obtains an X-ray image of the object and detects clinical information by performing image processing on the X-ray image. The X-ray apparatus may recognize the object included in the X-ray image by using image recognition and may detect clinical information about the object. In an embodiment, the controller 150 (see FIG. 3) may divide the X-ray image into an arbitrary number of regions and may recognize an amount of clinical information of the object included in each of the arbitrary number of regions. Also, the controller 150 may detect a region including a least amount of clinical information among the arbitrary number of regions.

In operation S1304, the X-ray apparatus determines a region whose clinical information in the X-ray image is not detected as a first region. However, embodiments are not limited thereto. In an embodiment, the controller 150 may determine the region including the least amount of clinical information of the object among the arbitrary number of regions detected in operation S1304 as a first region.

Figure 14:
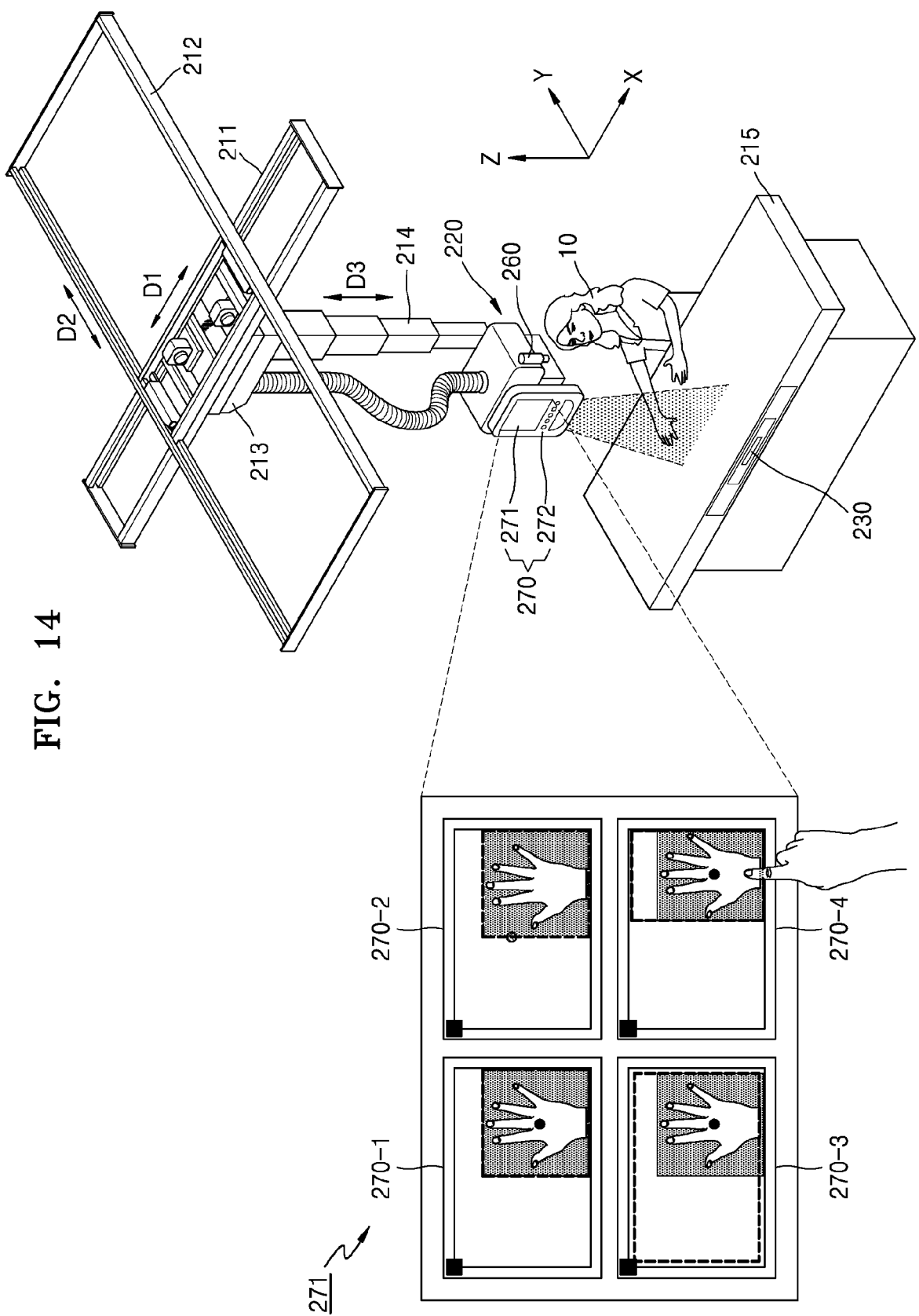
FIG. 14 is a conceptual view for explaining a method of adjusting positions of mechanical devices of an X-ray apparatus according to an embodiment.

In operation S1305, the X-ray apparatus combines the image marker with the first region. The X-ray apparatus may display the image marker so that the image marker overlaps the first region of the X-ray image of the object. FIG. 14 is a conceptual view for explaining a method of adjusting positions of mechanical devices of an X-ray apparatus 200 according to an embodiment.

Referring to FIG. 14, the X-ray apparatus 200 may include an X-ray emitter 220 that generates X-rays and radiates the X-rays to the object 10, an X-ray detector 230 that detects X-rays transmitted through the object 10, an image obtainer 260 that photographs the object 10 and obtains a captured image of the object 10, and a manipulator 270 that provides an interface for manipulating the X-ray apparatus 200. The X-ray emitter 220 and the X-ray detector 230 are respectively the same as the X-ray emitter 120 and the detector 130 of FIG. 1, and thus a repeated explanation thereof will not be provided.

The X-ray apparatus 200 may include motors each for applying a driving force for moving the X-ray emitter 220, and a first guide rail 211, a second guide rail 212, a movable carriage 213, and a post frame 214 that are provided to move the X-ray emitter 220 by using the driving forces of the respective third motors.

The first guide rail 211 and the second guide rail 212 are connected to intersect each other. The second guide rail 212 may be provided on the ceiling of an examination room. The first guide rail 211 may be disposed under the second guide rail 212, and may be slidably mounted on the second guide rail 212. A roller (not shown) that may move along the second guide rail 212 may be provided on the first guide rail 211. The first guide rail 211 may be connected to the roller and may move along the second guide rail 212. A first direction D1 is defined as a direction in which the first guide rail 211 extends, and a second direction D2 is defined as a direction in which the second guide rail 212 extends. Accordingly, the first direction D1 and the second direction D2 may intersect each other and may be parallel to the ceiling of the examination room.

The movable carriage 213 may be disposed under the first guide rail 211 to move along the first guide rail 211. A roller (not shown) that moves along the first guide rail 211 may be provided on the movable carriage 213. Accordingly, the movable carriage 213 may move in the first direction D1 along the first guide rail 211, and may move in the second direction D2 along the second guide rail 212.

The post frame 214 may be fixed to the movable carriage 213 and may be disposed under the movable carriage 213. In a state where the post frame 214 is fixed to the movable carriage 213, a length of the post frame 214 may be increased or reduced in a third direction D3. The third direction D3 may intersect both the first direction D1 and the second direction D2.

The X-ray emitter 220 is rotatably provided on a plane that is perpendicular to the ceiling of the examination room. A motor for moving the X-ray emitter 120 in each of the first through third directions D1 through D3 may be provided. The motor may be electrically driven, and may include an encoder.

The image obtainer 260 may be attached to a side of the X-ray emitter 220. The image obtainer 260 may obtain a captured image of the object 10 by photographing the object 10. The captured image of the object 10 obtained by the image obtainer 260 is different from an X-ray image obtained by X-ray imaging the object 10. The image obtainer 260 may be a camera for obtaining an image. In an embodiment, the image obtainer 260 may be attached to a side of a collimator 224 (see FIG. 20) of the X-ray emitter 220.

The manipulator 270 may be provided on a side surface of the X-ray emitter 220. The emitter 270 may include a display 271 and an input unit 272.

Although the X-ray apparatus 200 is a fixed X-ray apparatus connected to the ceiling of the examination room in FIG. 14, this is just for better understanding and embodiments are not limited to the fixed X-ray apparatus. Examples of the X-ray apparatus 200 may include various X-ray apparatuses, such as a C-arm X-ray apparatus and an angiography X-ray apparatus.

In an embodiment of FIG. 14, the X-ray apparatus 200 may control a position of the X-ray emitter 220 by performing image processing on a captured image of the object 10. In detail, the image obtainer 260 may obtain a captured image of the object 10 by photographing the object 10, and the X-ray apparatus 200 may recognize a region of the object 10 to be X-ray imaged (hereinafter, referred to as a candidate region of the object 10) and a central point of the object 10 by performing image processing on the obtained captured image, and may control an irradiation region shape of the X-ray emitter 220 and a position of the X-ray emitter 220 so that the recognized candidate region and the recognized central point of the object 10 are matched to an irradiation region of the X-ray emitter 220 and a central point of the X-ray emitter 220. In an embodiment, the X-ray apparatus 200 may display on the display 271 a UI for displaying information about the irradiation region of the X-ray emitter 220 and the central point of the X-ray emitter 220 to overlap the captured image. In an embodiment, the information about the irradiation region of the X-ray emitter 220 and the central point of the X-ray emitter 220 may be a plurality of combinations of information, and each of the plurality of combinations of information may overlap the captured image to form a plurality of thumbnail images, for example, first through fourth thumbnail images 270-1 through 270-4. The first through fourth thumbnail images 270-1 through 270-4 may be displayed on the display 271.

In an embodiment of FIG. 14, since the object 10 is photographed by using the image obtainer 260, that is, a camera, to obtain a captured image, a guide UI for controlling an irradiation region and a position of the X-ray emitter 220 is provided by performing image processing on the obtained captured image, and the X-ray emitter 220 is controlled according to an X-ray irradiation region and a position selected by a user (e.g., a radiologist or an examining doctor), a time taken to perform X-ray imaging may be minimized. Also, since the X-ray apparatus 200 according to an embodiment may reduce problems caused when a mechanical device is so heavy that the user feels pain in the shoulder or when the user has to manipulate a mechanical device whenever photographing is performed, photographing efficiency may be improved. Also, since the X-ray apparatus 200 according to an embodiment may control a position and an X-ray irradiation region of the X-ray emitter 220, the quality of an X-ray image may be improved.

A method of controlling an irradiation region and a position of the X-ray emitter 220 and a method of providing a guide UI in an image processing method of FIG. 14 will now be explained in detail with reference to FIGS. 15 through 19D.

Figure 15:
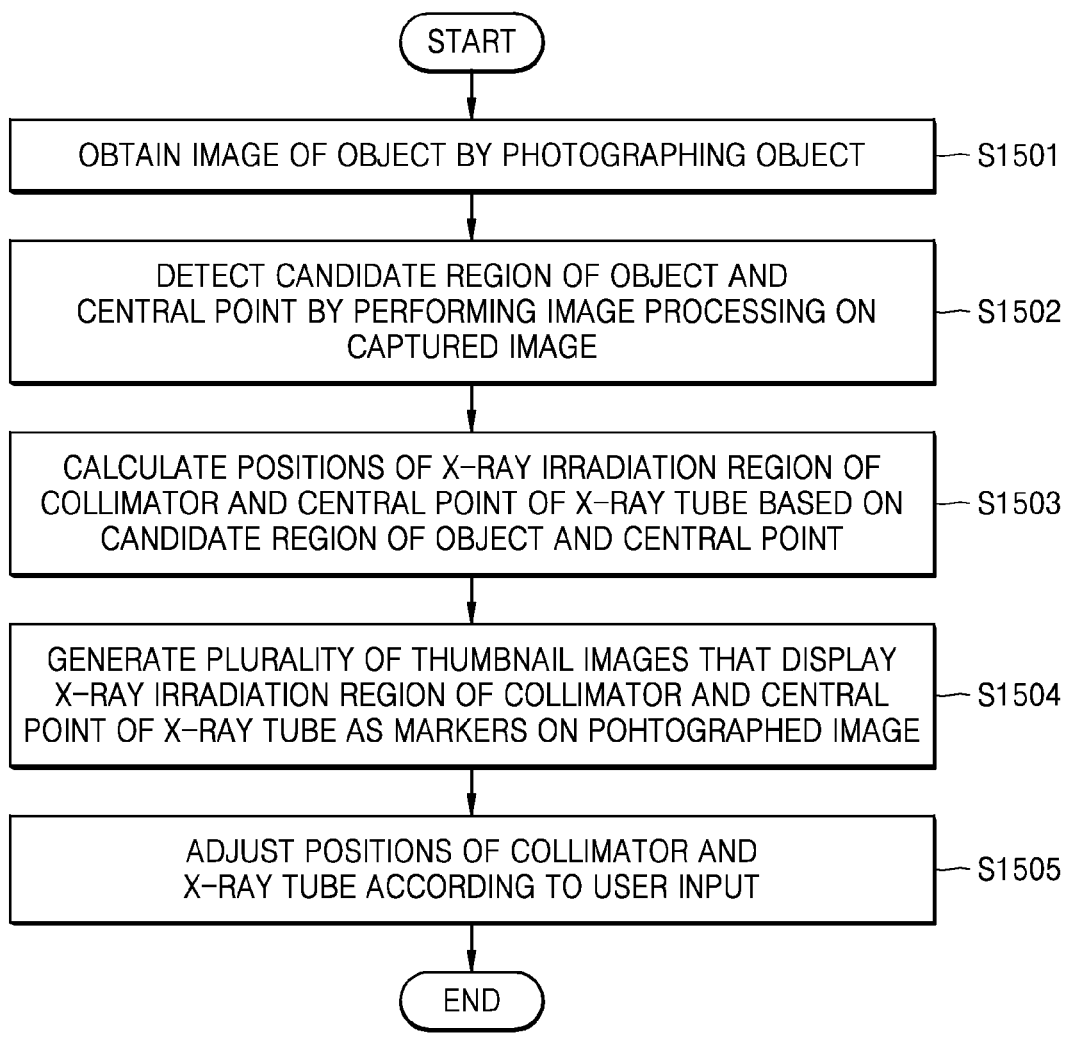
FIG. 15 is a flowchart of a method performed by the X-ray apparatus to adjust a position of a mechanical device according to an embodiment.

FIG. 15 is a flowchart of a method performed by the X-ray apparatus 200 of FIG. 14 to adjust a position of the X-ray emitter 220.

In operation S1501, the X-ray apparatus 200 (see FIG. 14) obtains a captured image of the object 10 by photographing the object 10. In an embodiment, the X-ray apparatus 200 may obtain a plurality of still images of the object 10 by continuously photographing the object 10. The captured image of the object 10 may be different from an X-ray image obtained by X-ray imaging the object 10. In an embodiment, the image obtainer 260 may determine only a region on the detector 230 (see FIG. 14), not the entire object 10, as a region of interest (ROI) and may photograph only a body part of the object 10 corresponding to the ROI.

In operation S1502, the X-ray apparatus 200 detects a candidate region of the object 10 and a central point of the object 10 by performing image processing on the captured image of the object 10. In an embodiment, the X-ray apparatus 200 may detect a candidate region of the object 10 and a central point of the object 10 by using any appropriate image analysis or image recognition algorithm. In an embodiment, the X-ray apparatus 200 may define a portion included in the ROI in the detector 230 (see FIG. 6) as a candidate region, and may detect a central point of a body part of the object included in the ROI. In an embodiment, the candidate region of the object 10 and the central point of the object 10 may overlap the captured image as a virtual graphical UI, and may be displayed on the display 271 (see FIG. 14).

In operation S1503, positions of an X-ray irradiation region of a collimator 224 (see FIG. 20) and a central point of an X-ray tube 222 (see FIG. 20) are calculated based on the candidate region of the object 10 and the central point of the object 10. In an embodiment, the X-ray apparatus 200 may calculate position values for respectively matching the X-ray irradiation region of the collimator 224 and the central point of the X-ray tube 222 to the candidate region of the object 10 and the central point of the object 10. The position values may be 2D coordinates values (x, y) or 3D coordinate values (x, y, z). The central point of the X-ray tube 222 and the central point of the object 10 may be displayed as markers on the captured image of the object 10. Also, the X-ray irradiation region of the collimator 224 and the candidate region of the object 10 may overlap the captured image as graphical UIs and may be displayed on the display 271.

A method of matching the candidate region of the object 10 and the central point of the object 10 to the X-ray irradiation region of the collimator 224 and the central point of the X-ray tube 222 may be performed in an embodiment, which will be explained below in detail with reference to FIGS. 16 through 19D.

In operation S1504, the first through fourth thumbnail images 270-1 through 270-4 in which the X-ray irradiation region of the collimator 224 (see FIG. 20) and the central point of the X-ray tube 222 (see FIG. 20) are displayed as graphical UIs are generated on the captured image. In an embodiment, information about the X-ray irradiation region of the collimator 224 and the central point of the X-ray tube 222 may be obtained by recognizing a shape or a size of the object by performing image processing on the captured image. In an embodiment, information about the X-ray irradiation region of the collimator 224 and the central point of the X-ray tube 222 may be obtained by using user experience-based learning data for analyzing a shutter-blade shape of the collimator 224 (see FIG. 20) that is frequently used by a user of the X-ray apparatus 200. In an embodiment, information about the X-ray irradiation region of the collimator 224 and the central point of the X-ray tube 222 may be obtained by using an imaging protocol of the object 10. In an embodiment, information about the X-ray irradiation region of the collimator 224 and the central point of the X-ray tube 222 may be obtained based on information (e.g., favorites information) previously input by the user.

A plurality of combinations of information may each overlap the captured image and thus the first through fourth thumbnail images 270-1 through 270-4 may be formed. The number of the first through fourth thumbnail images 270-1 through 270-4 is not limited to 4.

The information about the X-ray irradiation region of the collimator 224 and the central point of the X-ray tube 222 may be displayed on the display 271 to overlap the captured image as a marker having a virtual line or dot shape. However, embodiments are not limited thereto, and a UI for the information about the X-ray irradiation region of the collimator 224 and the central point of the X-ray tube 222 may not be displayed on the display 271 according to options set by the user of the X-ray apparatus 200.

In operation S1505, positions of the X-ray tube 222 (see FIG. 20) and the collimator 224 (see FIG. 20) are adjusted according to a user input. In an embodiment, the display 271 may include a touch screen including a touch pad that may receive a touch input of the user. In an embodiment, the display 271 may control a position of the X-ray emitter 220 (see FIG. 20) according to calculation values of the X-ray irradiation region of the collimator 224 and the central point of the X-ray tube 222 displayed on a thumbnail image selected by a user input among the first through fourth thumbnail images 270-1 through 270-4. In an embodiment, a shutter-blade of the collimator 224 may be adjusted in order to determine the X-ray irradiation region of the collimator 224 according to the calculation value displayed on the thumbnail image selected by the user input.

Figure 16:
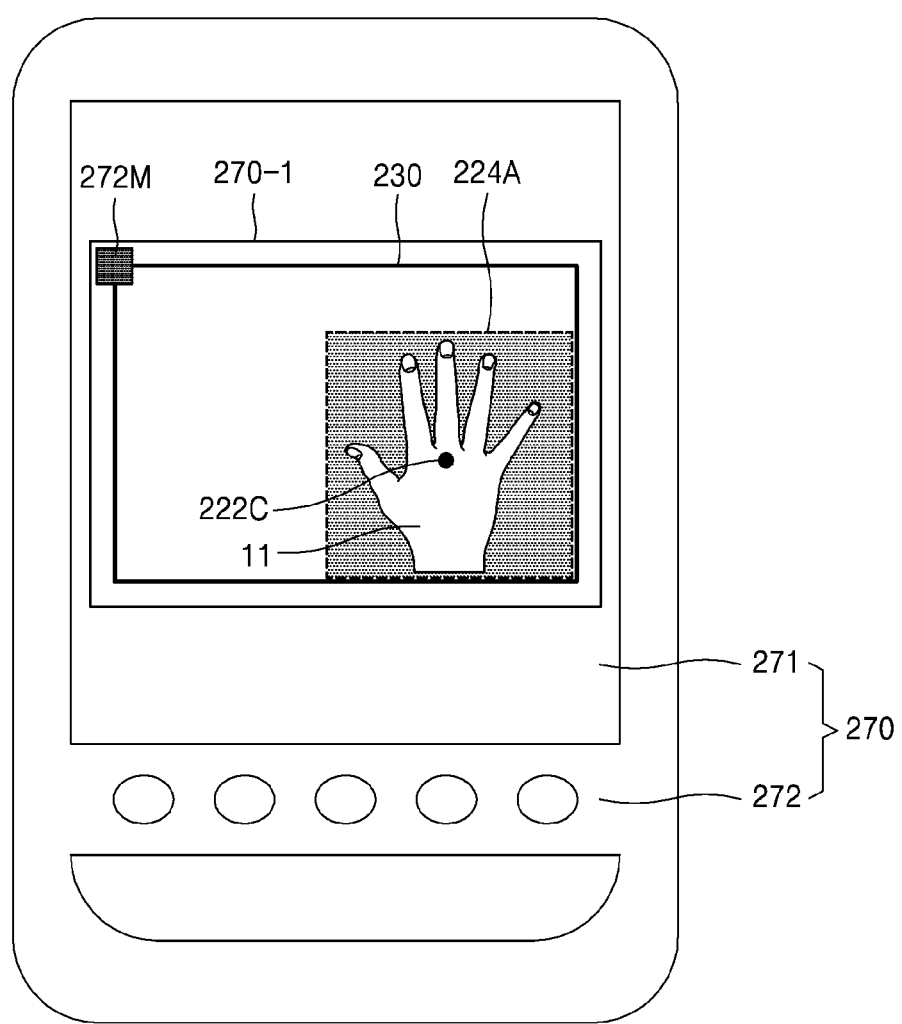
FIG. 16 is a view of a manipulator for displaying a mechanical device setting guide user interface (UI) according to an embodiment.

FIG. 16 is a view of the manipulator 270 for displaying a mechanical device setting guide UI according to an embodiment.

Referring to FIG. 16, the manipulator 270 may include the display 271 and the input unit 272. The display 271 may display the first thumbnail image 270-1. Examples of the display 271 may include a CRT display, an LCD display, a PDP display, an OLED display, an FED display, an LED display, a VFD display, a DLP display, an FPD display, a 3D display, and a transparent display.

A captured image of the object 10a, the detector 230, a central point marker 222C of an X-ray tube, an X-ray irradiation region 224A of a collimator, and a manual adjustment UI 272M may be displayed on the first thumbnail image 270-1. In an embodiment of FIG. 16, a target part of the object 10a, which is the hand of a patient, may be located on a right portion, instead of a central portion, of the detector 230. The captured image of the object 10a may be displayed to overlap the detector 230, and the X-ray irradiation region 224A of the collimator may be displayed on the detector 230 to overlap a candidate region of the captured image. A central point of the object 10a may be matched to a central point of the X-ray tube.

The manual adjustment UI 272M may enable a user of the X-ray apparatus 200 to directly adjust the X-ray irradiation region 224A of the collimator and the central point of the X-ray tube. In an embodiment, the manual adjustment UI 272M may be a touch UI that is supported by a touch screen.

FIGS. 17A through 19D are views for explaining a method of adjusting a mechanical device according to an embodiment.

Figure 17A:
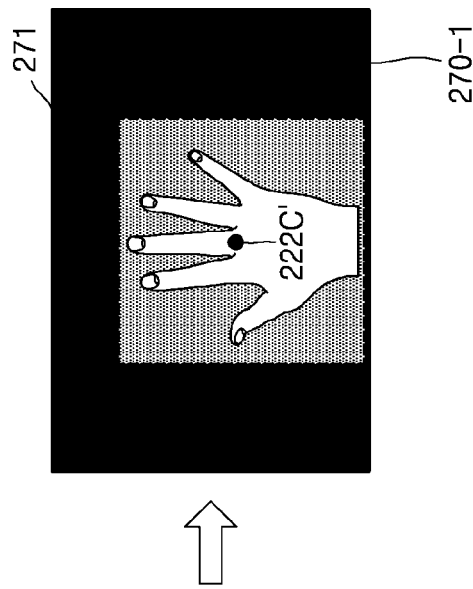
FIGS. 17A, 17B, and 17C are views for explaining a method of adjusting a mechanical device according to an embodiment.
Figure 17B:
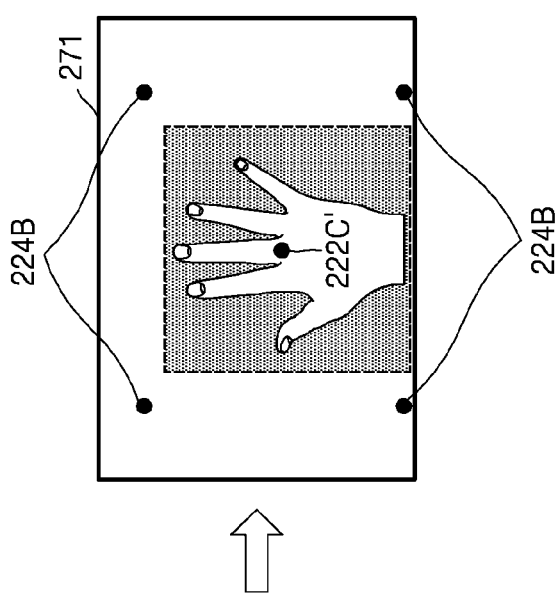
Figure 17C:
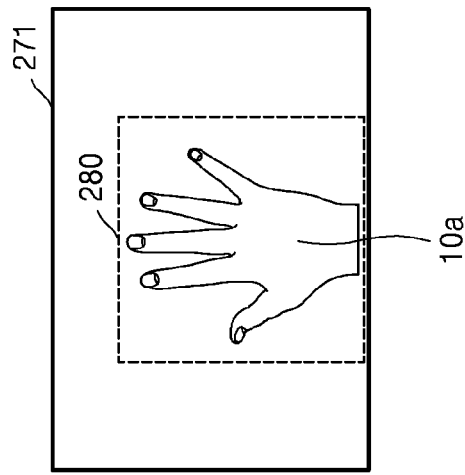

FIGS. 17A through 17C are views for explaining a method performed by the X-ray apparatus 200 to generate the first thumbnail image 270-1 for displaying a mechanical device setting guide UI based on coordinates. Referring to FIG. 17A, a captured image of the object 10a may be displayed on the display 271. A UI indicating an ROI may be displayed on the captured image.

Referring to FIG. 17B, the captured image of the object 10a, a central point marker 222C', and collimator coordinates 224B may be displayed on the display 271. The X-ray apparatus 200 may calculate coordinate values of a central point of the object 10a for calculating coordinates of a central point of an X-ray tube and the collimator coordinates 224b for calculating coordinates of an X-ray irradiation region of a collimator. In an embodiment, the collimator coordinates 224B may be coordinates that allow a shutter-blade for adjusting the X-ray irradiation region of the collimator to be adjusted. The collimator coordinates 224B and the central point of the object 10a may be displayed as a graphical UI to overlap the captured image of the object 10a.

Referring to FIG. 17C, the X-ray apparatus 200 may match the central point of the X-ray tube to the central point marker 222C' of the object 10a, and may generate the first thumbnail image 270-1 for adjusting the shutter-blade of the collimator based on the collimator coordinates 224B. In an embodiment, when a user of the X-ray apparatus 200 manipulates the X-ray tube 222 (see FIG. 20) or the collimator 224 (see FIG. 20), the first thumbnail image 270-1 may be updated in real time.

Figure 18C:
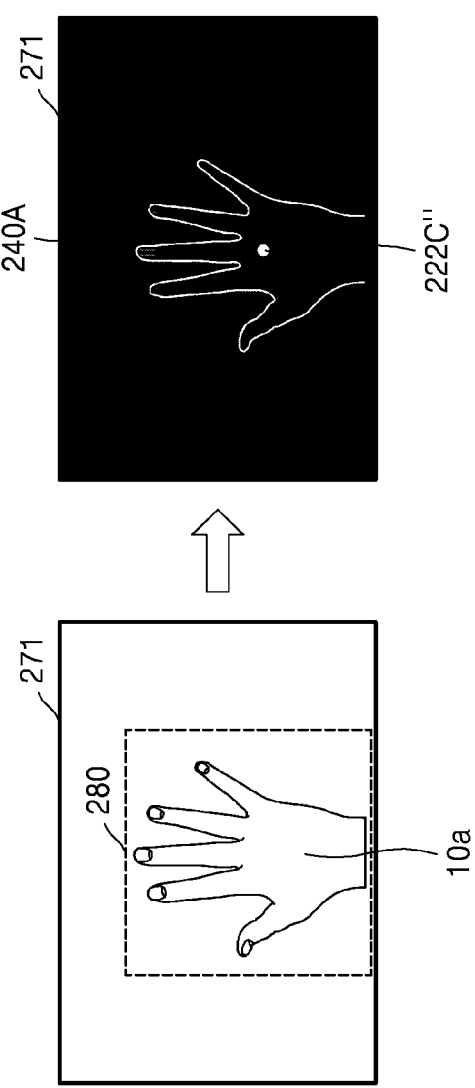
FIGS. 18A, 18B, and 18C are views for explaining a method of adjusting a mechanical device according to an embodiment.
Figure 18B:
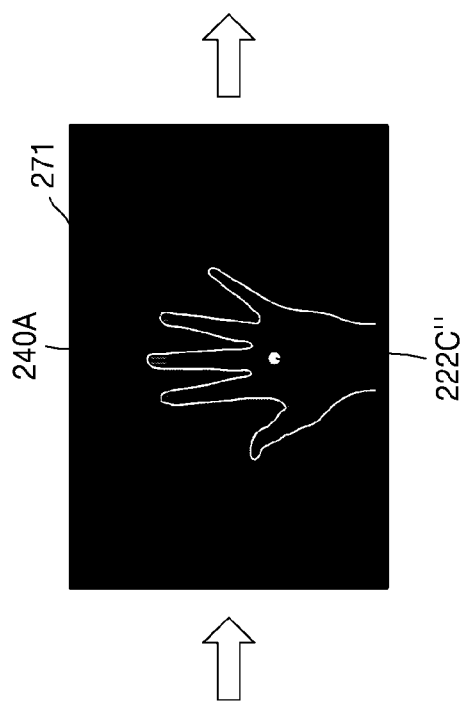
Figure 18A:
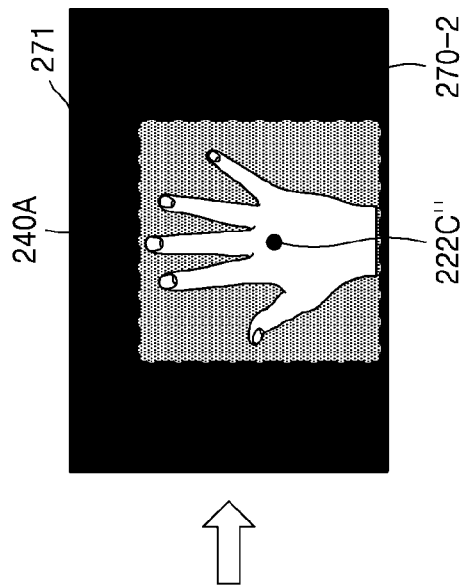

FIGS. 18A through 18C are views for explaining a method performed by the X-ray apparatus 200 to generate the second thumbnail image 270-2 for displaying a mechanical device setting guide UI by performing image processing on a captured image of the object 10a. Referring to FIG. 18A, the captured image of the object 10a may be displayed on the display 271. A UI indicating an ROI may be displayed on the captured image.

Referring to FIG. 18B, the captured image of the object 10a, a central point marker 222C", and an X-ray imaged region UI 240A may be displayed on the display 271. The X-ray apparatus 200 may recognize a central point of the object 10a and a candidate region of the object 10a by performing image processing on the captured image of the object 10a. In an embodiment of FIG. 18B, the X-ray apparatus 200 may recognize an outline and a shape of the hand of a patient by performing image processing on the captured image including the hand and may detect a central point and an outer region of the hand, that is, a to-be X-ray imaged region, according to the recognized outline and the recognized shape of the hand.

Referring to FIG. 18C, the X-ray apparatus 200 may generate the second thumbnail image 270-2 including the central point marker 222C" of the object 10a and the X-ray imaged region UI 240A. In an embodiment, the X-ray apparatus 200 may control a central point of the X-ray tube 222 (see FIG. 20) to be matched to the central point marker 222C" and a shutter-blade of the collimator 224 (see FIG. 20) to be matched to the X-ray imaged region UI 240A.

Figure 19C:
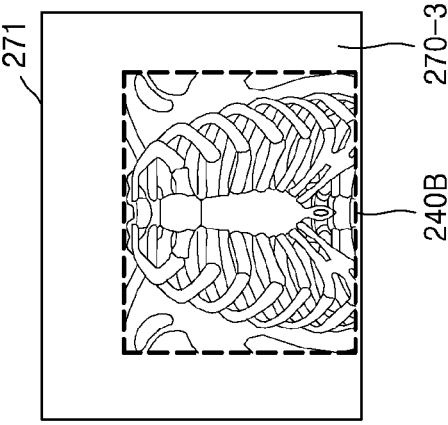
FIGS. 19A, 19B, 19C, and 19D are views for explaining a method of adjusting a mechanical device according to an embodiment.
Figure 19D:
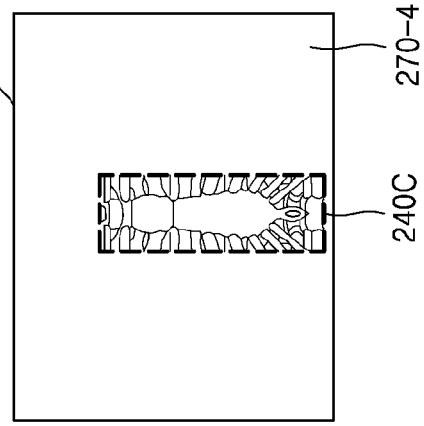
Figure 19B:
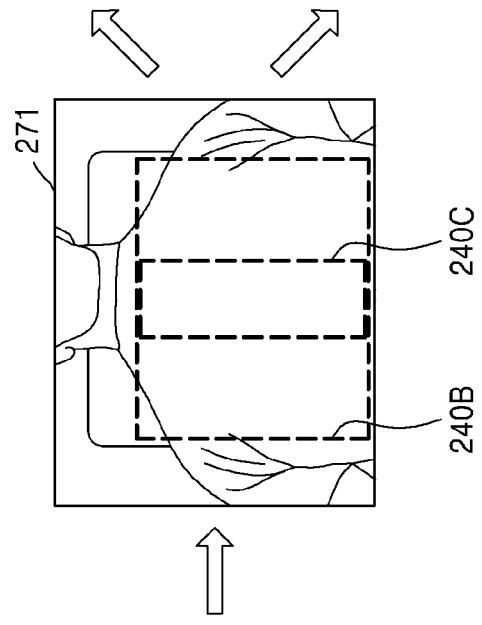
Figure 19A:
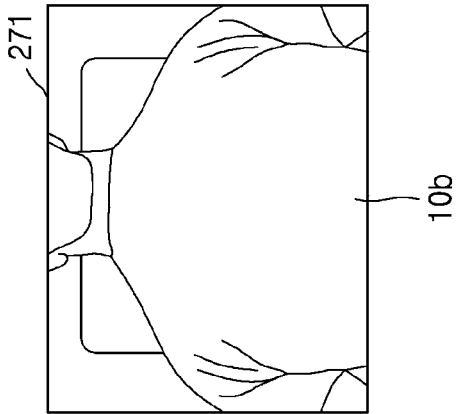

FIGS. 19A through 19D are views for explaining a method performed by the X-ray apparatus 200 to generate the third thumbnail image 270-3 and the fourth thumbnail image 270-4 based on user experience-based learning data of an object 10b. Different guide UIs may be displayed on the third thumbnail image 270-3 and the fourth thumbnail image 270-4 according to an imaging protocol. Referring to FIG. 19A, a captured image of the object 10b may be displayed on the display 271.

Referring to FIG. 19B, UIs for the captured image of the object 10b, a first candidate region 240B, and a second candidate region 240C may be displayed on the display 271. The X-ray apparatus 200 may display a UI when the first candidate region 240B is matched to a shutter-blade of the collimator 224 (see FIG. 20) or when the second candidate region 240C is matched to the shutter-blade of the collimator 224 according an imaging protocol of the object 10b may be displayed to overlap the captured image of the object 10b. In FIG. 19B, the L-spine of a patient is photographed. The shutter-blade of the collimator 224 may be photographed to show the whole body of the patient (e.g., the first candidate region 240B) or to narrowly and longitudinally show mainly the spine of the patient (e.g., the second candidate region 240C).

FIG. 19C is a view illustrating the third thumbnail image 270-3 that provides a guide UI when the shutter-blade of the collimator 224 (see FIG. 20) is matched to the first candidate region 240B on the captured image of the object. FIG. 19D is a view illustrating the fourth thumbnail image 270-4 that provides a guide UI when the shutter-blade of the collimator 224 is matched to the second candidate region 240C. In an embodiment, the third thumbnail image 270-3 is a guide image for setting the shutter-blade of the collimator 224 to X-ray image the whole body of the patient, and the fourth thumbnail image 270-4 is a guide image for setting the shutter-blade of the collimator 224 to longitudinally X-ray image the spine (L-spine) of the patient. In an embodiment, the third thumbnail image 270-3 and the fourth thumbnail image 270-4 may be generated by obtaining data about a shutter-blade shape of the collimator 224 that is frequently used when a user (e.g., a radiologist) of the X-ray apparatus 200 X-ray images the object 10b according to an imaging protocol and by obtaining user experience-based learning data for analyzing the shutter blade shape preferred by the user. In an embodiment, the third thumbnail image 270-3 and the fourth thumbnail image 270-4 may display a UI for distinguishing a priority based on the user experience-based learning data. The UI for distinguishing the priority may include at least one among a text, a color, and a marker.

Figure 20:
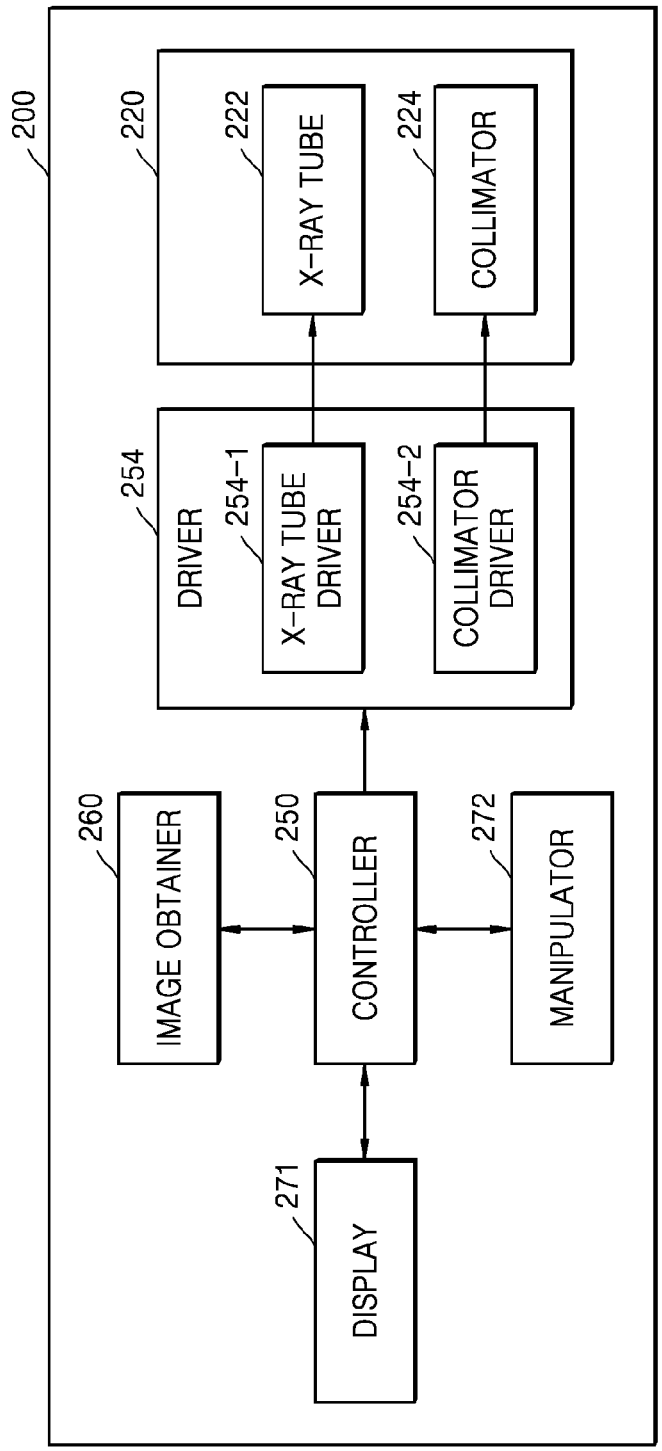
FIG. 20 is a block diagram of the X-ray apparatus according to an embodiment.

FIG. 20 is a block diagram of the X-ray apparatus 200 according to an embodiment.

Referring to FIG. 20, the X-ray apparatus 200 may include the X-ray emitter 220, a controller 250, a driver 254, the image obtainer 260, the display 271, and the manipulator 272. The X-ray emitter 220 may include the X-ray tube 222 and the collimator 224. The X-ray tube 222 and the collimator 224 are respectively the same as the X-ray source 122 and the collimator 123 of FIG. 1, and thus a repeated explanation thereof will not be provided.

The image obtainer 260 may obtain a captured image of an object by photographing the object. The image obtainer 260 may be attached to a side of the collimator 224. The image obtainer 260 may include a camera. The camera may be disposed to face the object, and may include a camera sensor configured to convert an image of the object into an electrical signal and a signal processor configured to convert an analog image signal obtained from the camera sensor into a digital signal. The camera sensor may be a CCD or CMOS sensor, and the signal processor may be a DSP. The captured image of the object obtained by the image obtainer 260 is different from an X-ray image obtained by X-ray imaging the object.

The controller 250 may recognize a candidate region of the object and a central point of the object by performing image processing on the captured image obtained by the image obtainer 260 by photographing the object, and may generate a thumbnail image by causing UIs indicating a central point of the X-ray emitter 220 and an irradiation region shape of the X-ray emitter 220 to overlap the recognized candidate region and the recognized central point of the object. The controller 250 may include a hardware element such as an FPGA or an ASIC. For example, the controller 250 may be a hardware device including at least one among hardware units including a CPU, a microprocessor, and a GPU. The controller 250 may include an image processor for performing image processing such as image recognition or image analysis based on appropriate software and/or algorithms known to those skilled in the art.

In an embodiment, the controller 250 may generate a thumbnail image by causing graphical UIs indicating a shutter-blade region of the collimator 224 and a central point of the X-ray tube 222 to overlap the candidate region of the object and the central point of the object recognized by performing image processing on the captured image. In an embodiment, there may be a plurality of shutter-blade shapes of the collimator 224 and a plurality of central points of the X-ray tube 222 respectively matched to the candidate region of the object and the central point of the object, and the controller 250 may generate a plurality of thumbnail images by causing the plurality of shutter-blade shapes of the collimator 224 and the plurality of central points of the X-ray tube 222 to each overlap the captured image.

The controller 250 may calculate a shape of an X-ray irradiation region of the X-ray emitter 220 and a position of a central point respectively matched to the candidate region of the object and the central point of the object, and may control the X-ray emitter 220. The controller 250 may control a position of the X-ray tube 222 so that a central point of the X-ray tube 222 is matched to the central point of the object recognized by performing image processing on the captured image, and may control the collimator 224 so that a shape of the X-ray irradiation region, that is, a shutter-blade, of the collimator 224 is matched to the candidate region of the object.

In an embodiment, the controller 250 may calculate target position values to match the candidate region of the object and the central point of the object to the X-ray irradiation region of the collimator 224 and the central point of the X-ray tube 222. The position values may be 2D coordinates (x, y) or 3D coordinates (x, y, z). Also, the controller 250 may calculate a position control amount to match the central point of the X-ray tube 222 to the central point of the object.

In an embodiment, the controller 250 may calculate a shutter-blade shape of the collimator 224 and a position of the central point of the X-ray tube 222 based on information about a shape and a size of the object. In detail, the controller 250 may recognize the candidate region and the central point of the object suitable for the shape and the size of the object by performing image analysis on the captured image of the object, and may control the shutter-blade shape of the collimator 224 and the position of the central point of the X-ray tube 222 to be matched to the candidate region of the object and the central point of the object recognized by performing image analysis.

In an embodiment, the controller 250 may obtain the shutter-blade shape of the collimator 224 that is frequently used by a user of the X-ray apparatus 200 based on user experience-based learning data for analyzing the shutter-blade shape of the collimator 224. The controller 250 may recognize the shutter-blade shape of the collimator preferred by the user according to an imaging protocol for photographing the object by analyzing a shape of the shutter-blade of the collimator 224 that is used by the user according to the imaging protocol and the number of times the shape is used.

In an embodiment, the controller 250 may control the shutter-blade shape of the collimator 224 and the position of the central point of the X-ray tube 222 based on information (e.g., favorites information) previously input by the user of the X-ray apparatus 200.

Although the controller 250 is an element included in the X-ray apparatus 200 in FIG. 20, embodiments are not limited thereto. In an embodiment, the controller 250 may be included in a workstation. In this case, the workstation may control the driver 254, the image obtainer 260, the display 271, and the manipulator 272 of the X-ray apparatus 200 by using the controller 250.

The driver 254 may drive the X-ray emitter 220 to a specific position on the object according to position information values calculated by the controller 250. The driver 254 may include an X-ray tube driver 254-1 and a collimator driver 254-2. The X-ray tube driver 254-1 may be a driving device such as a motor, and may adjust a position of the X-ray tube 222 according to a position control value and a target position value for matching the central point of the X-ray tube 222 calculated by the controller 250 to the central point of the object. The collimator driver 254-2 may adjust the collimator 224 according to the shutter-blade shape of the collimator 224 matched to the candidate region of the object calculated by the controller 250.

The display 271 may output a thumbnail image generated by the controller 250. In an embodiment, the display 271 may output a plurality of thumbnail images. In an embodiment, the display 271 may include at least one among a CRT display, an LCD display, a PDP display, an OLED display, an FED display, an LED display, a VFD display, a DLP display, an FPD display, a 3D display, and a transparent display. In an embodiment, the display 271 may be a touch screen that receives a touch input of the user that selects any one among the plurality of thumbnail images displayed on the display 271. The manipulator 272 may be a button for manipulating a function of the X-ray apparatus 200.

Figure 21:
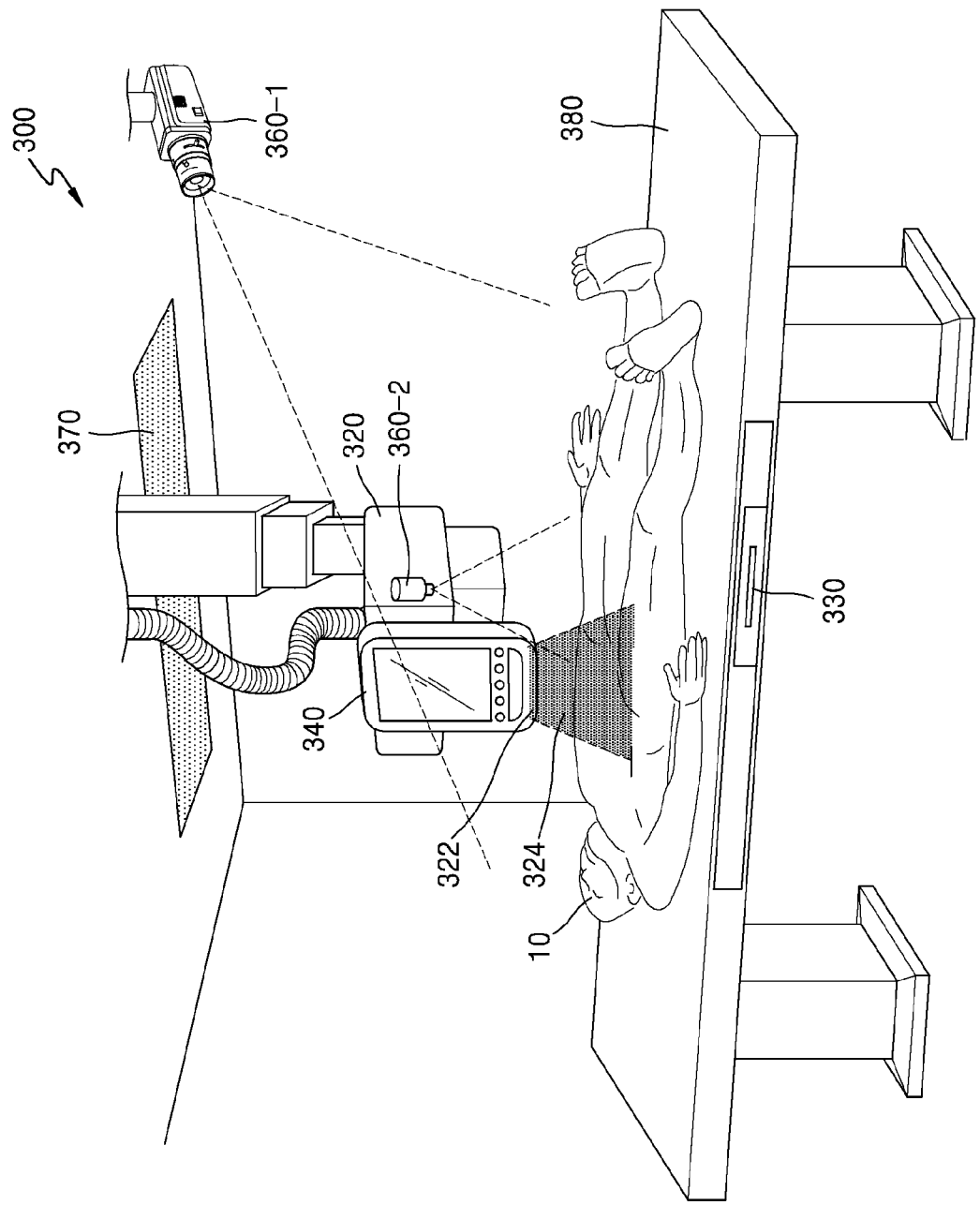
FIG. 21 is a conceptual view for explaining a method performed by an X-ray apparatus to control an X-ray imaging condition by performing image processing on an image obtained by photographing an object according to an embodiment.

FIG. 21 is a conceptual view for explaining a method performed by an X-ray apparatus 300 to control an X-ray imaging condition by performing image processing on a captured image obtained by photographing the object 10 according to an embodiment.

Referring to FIG. 21, the X-ray apparatus 300 may include an X-ray emitter 320, a collimator light source 322, a detector 330, a manipulator 340, a first camera 360-1, a second camera 360-2, and a table 380. In an embodiment, the X-ray apparatus 300 may further include an examination room light source 370. The X-ray emitter 320, the detector 330, and the manipulator 340 are respectively the same as the X-ray emitter 120, the detector 130, and the manipulator 140 of FIG. 1, and thus a repeated explanation thereof will not be provided.

The first camera 360-1 may be attached to an examination room in which the X-ray apparatus 300 is located. The first camera 360-1 may be attached to the ceiling of the examination room, and may be an apparatus for obtaining an image. The first camera 360-1 may photograph the entire examination room or the object 10, and may obtain a captured image of the entire examination room or the object 10.

The second camera 360-2 may be attached to a side of the X-ray emitter 320. In an embodiment, the second camera 360-2 may be attached to a collimator of the X-ray emitter 320. The second camera 360-2 may photograph the object 10 and a candidate region of the object 10 and may obtain captured images of the object 10 and the candidate region of the object 10.

The collimator light source 322 may be formed on a side of the X-ray emitter 320 and may include an LED light source. In an embodiment, the collimator light source 322 may be integrally formed with the collimator of the X-ray emitter 320. The collimator light source 322 may emit LED light 324 to the candidate region of the object 10. The LED light 324 may have a specific color.

The examination room light source 370 may be attached to the ceiling of the examination room in which the X-ray apparatus 300 is located, and may include an LED light source.

The X-ray apparatus 300 of FIG. 21 may photograph an imaging environment of the examination room in which the object 10 or the X-ray apparatus 300 is located by using the first camera 360-1 and/or the second camera 360-2 to obtain a captured image, may detect an imaging condition including a luminance and a color of an X-ray irradiation region of the object 10 and/or the examination room by performing image processing on the captured image, and may automatically set imaging options including a luminance and a color of the collimator light source 322 and/or the examination room light source 370 according to the detected imaging condition. In detail, the X-ray apparatus 300 may detect a luminance of the entire examination room by performing image processing on an examination room captured image obtained by photographing the examination room by using the first camera 360-1, and may detect a movement of the object 10 or a user 20 (see FIGS. 24A and 24B) in the examination room. The X-ray apparatus 300 may detect a luminance and a color of an ambient area of the object 10 and an X-ray irradiation region of the object 10 by performing image processing on a captured image of the object 10 obtained by photographing the object 10 by using the second camera 360-2. The ambient area of the object 10 may be at least one among the detector 330, the table 380, and the entire examination room. In an embodiment, the X-ray apparatus 300 may recognize a luminance difference between the X-ray irradiation region of the object 10 and the ambient area of the object 10 by performing image processing on the captured images obtained by using the first camera 360-1 and the second camera 360-2, and may control the collimator 322 or the examination room light source 370 according to the luminance difference.

In an embodiment of FIG. 21, since the X-ray apparatus 300 may automatically set imaging options of the X-ray apparatus 300, that is, the examination room light source 370 and/or the collimator light source 322, according to an imaging condition including a luminance of the examination room and luminance values of the object 10 and the ambient area of the object 10, user convenience may be improved. Also, a collimated region may be accurately set. The embodiment of FIG. 21 may apply to other medical imaging apparatuses as well as the X-ray apparatus 300.

Figure 22:
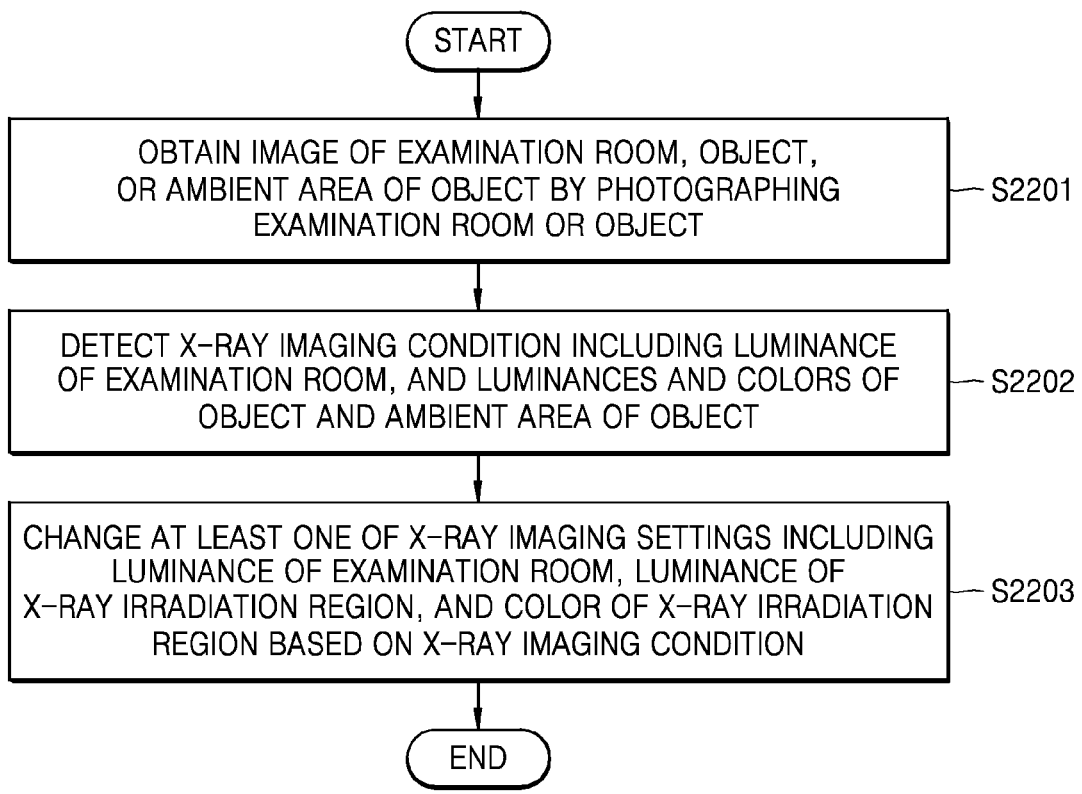
FIG. 22 is a flowchart of a method performed by the X-ray apparatus of FIG. 21 to change imaging option settings according to an imaging condition.

FIG. 22 is a flowchart of a method performed by the X-ray apparatus 300 of FIG. 21 to change imaging option settings according to an imaging condition.

In operation S2201, the X-ray apparatus 300 obtains a captured image of an examination room, an object, or an ambient area of the object by photographing the examination room or the object. In an embodiment, the ambient area of the object may include at least one among the detector 330 (see FIG. 21) on which the object is placed, the table 380 (see FIG. 21), and a candidate region of the object. The captured image may be different from an X-ray image obtained by X-ray imaging the object. In an embodiment, the captured image of the examination room may be obtained by using the first camera 360-1 (see FIG. 21) and the captured image of the object or the ambient area of the object may be obtained by using the second camera 360-2.

In operation S2202, the X-ray apparatus 300 detects an X-ray imaging condition including a luminance of the examination room, and luminances and colors of the object and the ambient area of the object by performing image processing on the captured image. The X-ray apparatus 300 may detect the X-ray imaging condition by performing image recognition on the captured image based on appropriate software and/or algorithms known to those skilled in the art. In an embodiment, the X-ray apparatus 300 may obtain information about the luminance of the examination room by applying image recognition to the captured image of the examination room obtained by photographing the examination room. Also, the X-ray apparatus 300 may obtain information about the luminances and colors of the object and/or the ambient area of the object by applying image recognition to the captured image of the object obtained by photographing the object. In an embodiment, the X-ray apparatus 300 may detect the color of the ambient area of the object, for example, the detector 330 (see FIG. 21), the table 380 (see FIG. 21), and a mechanical device including a stand, by performing image processing on the captured image of the ambient area of the object by photographing the ambient area of the object.

In operation S2203, the X-ray apparatus 300 changes at least one among X-ray imaging option settings including the luminance of the examination room, a luminance of an X-ray irradiation region, and a color of the X-ray irradiation region based on the X-ray imaging condition. In an embodiment, the X-ray apparatus 300 may change setting values of a luminance and a color of the collimator light source 322 and/or the examination room light source 370 (see FIG. 21) based on a difference between the luminance of the examination room and the luminance of the X-ray irradiation region. In an embodiment, the X-ray apparatus 300 may detect a position of a user or a behavior or an action of the user who, for example, may be performing an action of adjusting the collimator, and may change setting values of a luminance and a color of the collimator light source 322 and/or the examination room light source 370 (see FIG. 21). In an embodiment, the X-ray apparatus 300 may change a color of LED light of the collimator light source 322 when it is determined that the color of the object is similar to the color of the ambient area of the object.

Figure 23:
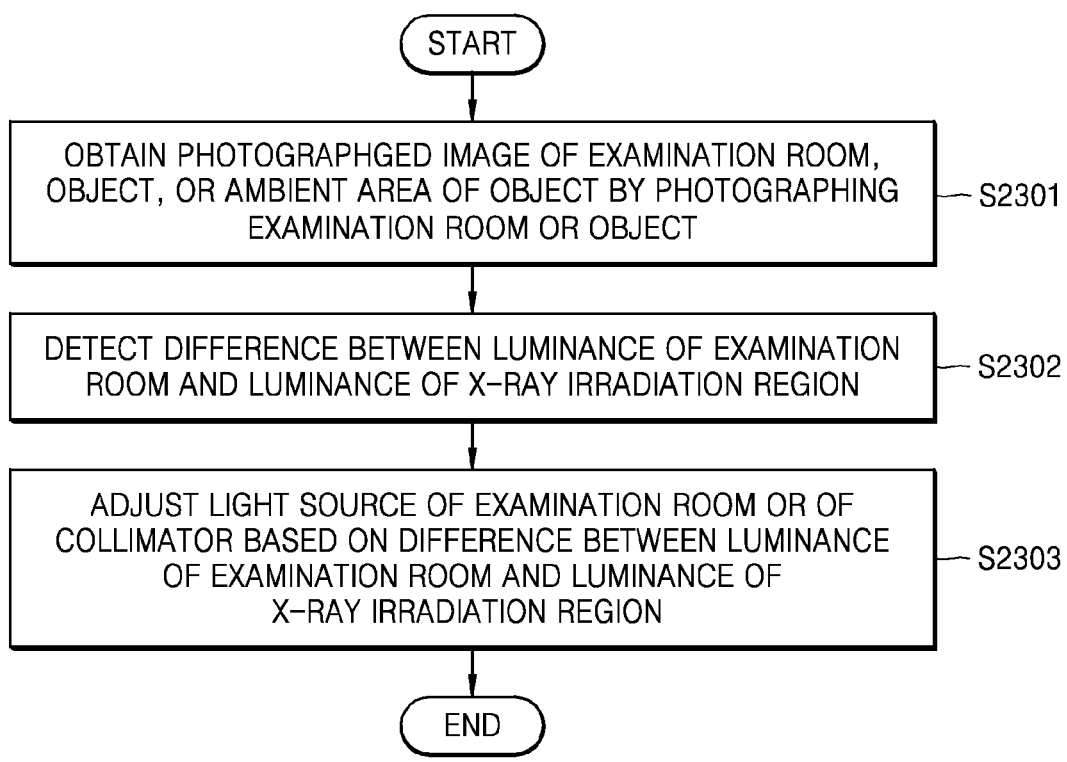
FIG. 23 is a flowchart of a method performed by the X-ray apparatus to change imaging settings according to a luminance of an examination room and a luminance of an X-ray irradiation region according to an embodiment.

FIG. 23 is a flowchart of a method performed by the X-ray apparatus 300 of FIG. 21 to change imaging settings according to a luminance of an examination room and a luminance of an X-ray irradiation region.

In operation S2301, the X-ray apparatus 300 obtains a captured image of an examination room, an object, or an ambient area of the object by photographing the examination room or the object. The obtaining of the captured image performed in operation S2501 is the same as that described in operation S2201 of FIG. 22, and thus a repeated explanation thereof will not be provided.

In operation S2302, the X-ray apparatus 300 detects a difference between a luminance of the examination room and a luminance of an X-ray irradiation region according to X-rays radiated to the object by performing image processing on the captured image. In an embodiment, the X-ray apparatus 300 may obtain information about the luminance of the examination room by applying image recognition to the captured image of the examination room obtained by the first camera 360-1, and may obtain information about the luminance of the X-ray irradiation region of the object by applying image recognition to the captured image of the object including the X-ray irradiation region of the object obtained by the second camera 360-2.

In operation S2303, the X-ray apparatus 300 adjusts the examination room light source 370 (see FIG. 21) or the collimator light source 322 (see FIG. 21) based on the difference between the luminance of the examination room and the luminance of the X-ray irradiation region. In an embodiment, when a difference between the luminance of the examination room and a luminance of an ambient area of the object is so small that a user might not recognize the difference with the naked eye, the X-ray apparatus 300 may adjust a brightness of the collimator light source 322 to a higher level, and may adjust a brightness of the examination room light source 370 to a lower level.

Figure 24A:
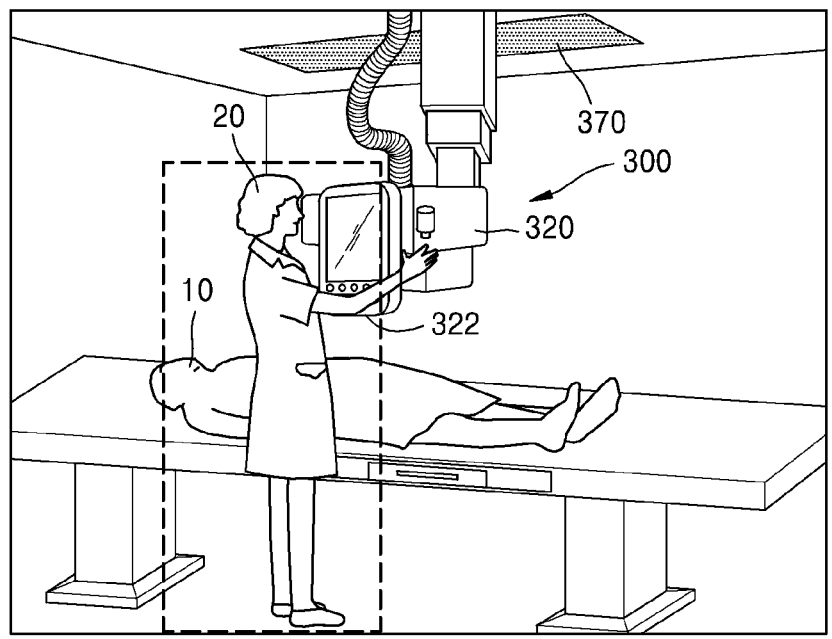
FIGS. 24A and 24B are views for explaining a method performed by the X-ray apparatus of FIG. 21 to control imaging option settings by recognizing a behavior of a user and a behavior of the object.
Figure 24B:
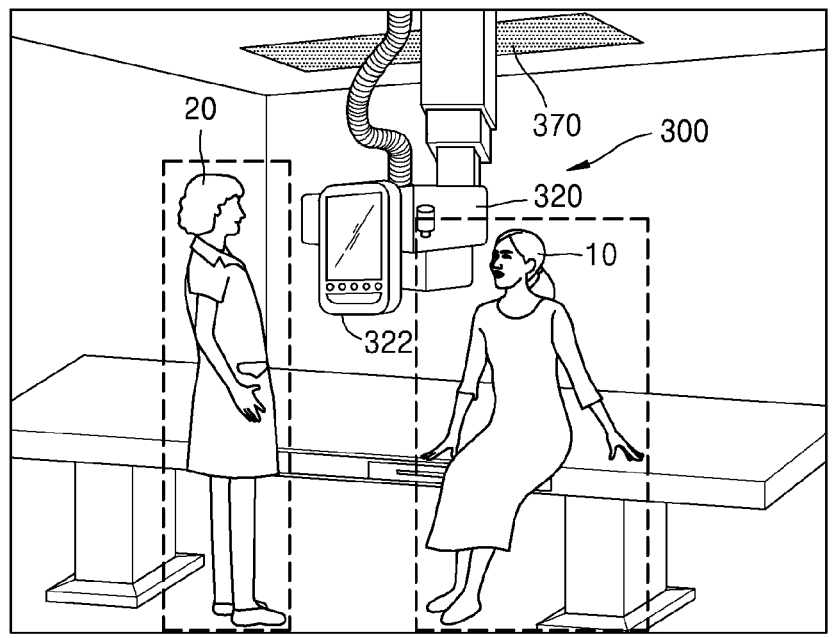
Figure 25:
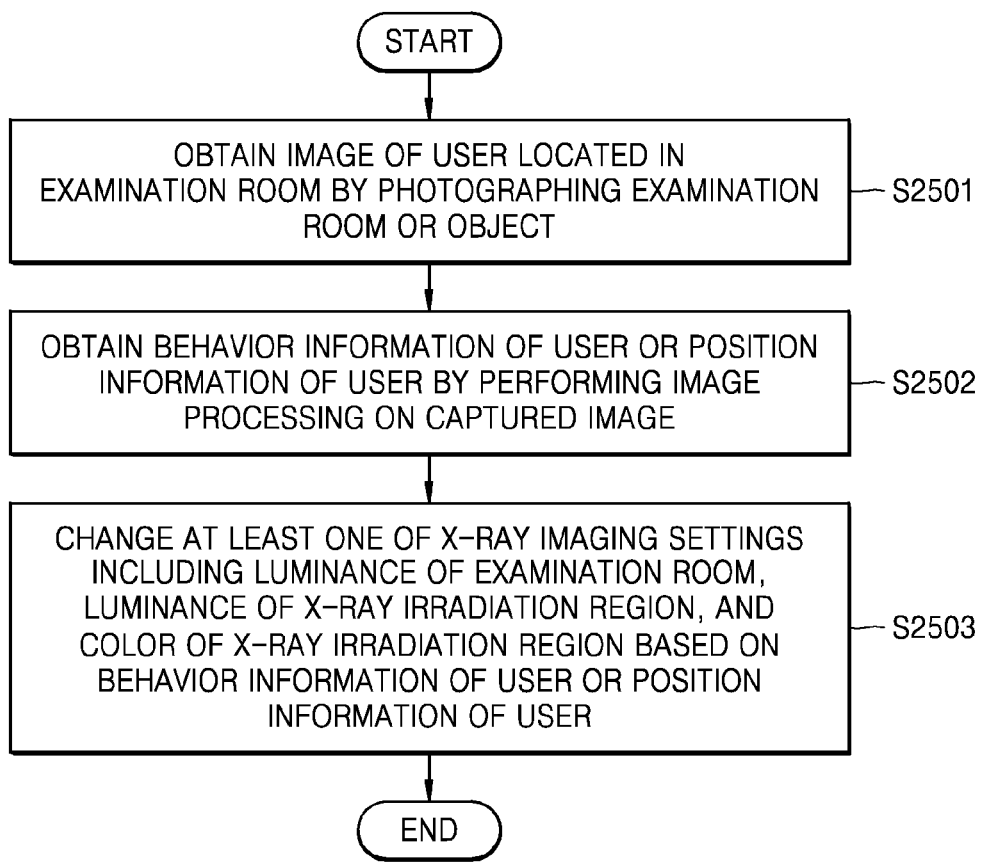
FIG. 25 is a flowchart of the method of FIGS. 24A and 24B.

FIGS. 24A and 24B are views for explaining a method performed by the X-ray apparatus 300 to control imaging option settings by identifying a behavior or an action of the user 20 of the X-ray apparatus 300 and a behavior or an action of the object 10. FIG. 25 is a flowchart of the method of FIGS. 24A and 24B.

In operation S2501, the X-ray apparatus 300 obtains a captured image of the user 20 who is located in an examination room by photographing the examination room or the object 10. Referring to FIGS. 24A and 24B, the user 20 of the X-ray apparatus 300 may be, for example, a radiologist or an examining doctor. Except that the user 20 is located in the examination room, the obtaining of a captured image of the examination room is the same as that described in operation S2201, and thus a repeated explanation thereof will not be provided.

In operation S2502, the X-ray apparatus 300 obtains behavior information of the user 20 or position information of the user 20 by performing image processing on the captured image. In an embodiment, the X-ray apparatus 300 may recognize the position information or the behavior information of the user 20 included in the captured image by using image recognition based on appropriate software and/or algorithms known to those skilled in the art. Referring to FIG. 24A, the X-ray apparatus 300 may recognize an action of the user 20 who manipulates the X-ray emitter 320. In an embodiment, the user 20 may perform an action of adjusting an X-ray irradiation region of the object 10 by manipulating a shutter-blade of a collimator, and the X-ray apparatus 300 may recognize the behavior of the user 20 by using image recognition. Referring to FIG. 24B, the X-ray apparatus 300 may determine that the user 20 who stands up performs an action of talking to the object 10. In FIG. 24B, the action of the user 20 who is standing and taking to the object 10 may mean that X-ray imaging has ended. In an embodiment, the X-ray apparatus 300 may recognize an action of the object 10 as well as a behavior of the user 20. In an embodiment, the X-ray apparatus 300 may recognize a current position of the user 20, that is, information about whether the user 20 is located in front of a door of the examination room or in front of the X-ray apparatus 300.

In operation S2503, at least one among X-ray imaging option settings including a luminance of the examination room, a luminance of the X-ray irradiation region, and a color of the X-ray irradiation region is changed based on the position information of the user 20 or the behavior information of the user 20. Referring to FIG. 24A, the X-ray apparatus 300 may recognize that user 20 performs an action of manipulating the shutter-blade of the collimator, may determine that the X-ray imaging is about to begin, and may control a brightness of the collimator light source 322 (see FIG. 21) to be increased and a brightness of the examination room light source 370 (see FIG. 21) to be reduced. Referring to FIG. 24B, the X-ray apparatus 300 may recognize that the user 20 is spaced apart by a predetermined distance from the X-ray apparatus 300 and the object 10 sits up and talks to the user 20, may determine that the X-ray imaging has ended, and may control a brightness of the collimator light source 322 to be reduced and a brightness of the examination room light source 370 to be increased. In an embodiment, a brightness of the examination room light source 370 may be controlled according to a section or the whole of the examination room.

Figure 26:
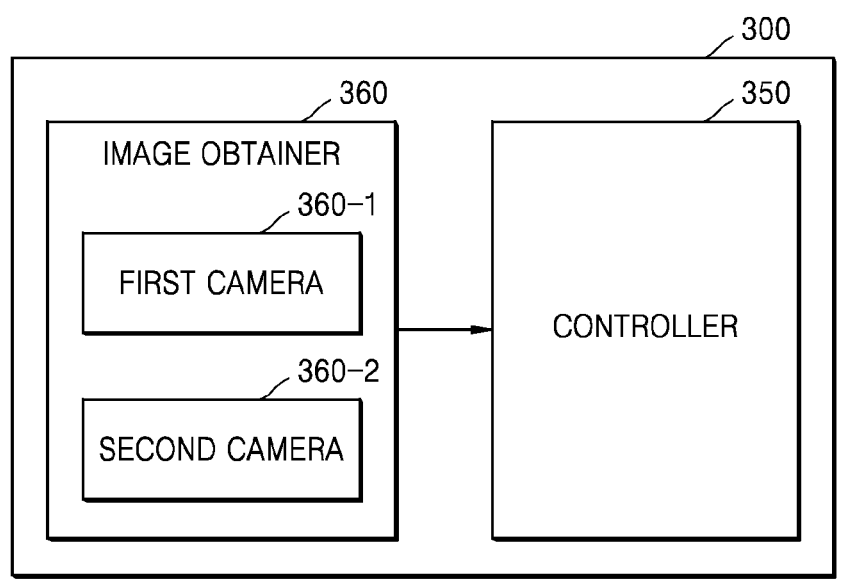
FIG. 26 is a block diagram of the X-ray apparatus according to an embodiment.

FIG. 26 is a block diagram of the X-ray apparatus 300 according to an embodiment.

Referring to FIG. 26, the X-ray apparatus 300 may include a controller 350 and an image obtainer 360. The image obtainer 360 may include the first camera 360-1 (see FIG. 21) and the second camera 360-2 (see FIG. 21). The first camera 360-1 and the second camera 360-2 are the same as those in FIG. 21, and thus a repeated explanation thereof will not be provided. Although the X-ray apparatus 300 includes only the controller 350 and the image obtainer 360 in FIG. 26, embodiments are not limited thereto. The X-ray apparatus 300 may further include the X-ray emitter 320, the collimator light source 322, the detector 330, the manipulator 340, and the table 380 (see FIG. 21). The X-ray emitter 320, the collimator light source 322, the detector 330, the manipulator 340, and the table 380 are the same as those in FIG. 21, and thus a repeated explanation thereof will not be provided.

The controller 350 may detect a luminance of an examination room, and luminances and colors of an object and an ambient area of the object by performing image processing on a captured image obtained by the image obtainer 360 by photographing the examination room, the object, or the ambient area of the object. The controller 350 may be a hardware device for performing image processing, for example, image recognition. For example, the controller 350 may be a hardware device including at least one among a CPU, a microprocessor, and a GPU. Although the controller 350 is an element included in the X-ray apparatus 300 in FIG. 26, embodiments are not limited thereto. In an embodiment, the controller 350 may be included in a workstation.

In an embodiment, the controller 350 may detect a difference between the luminance of the examination room and a luminance of an X-ray irradiation region according to X-rays radiated to the object by performing image processing on the captured image. In an embodiment, the controller 350 may recognize position information or behavior information of a user included in the captured image of the examination room by performing image recognition on the captured image of the examination room obtained by photographing the examination room. In an embodiment, the controller 350 may detect a behavior of the user who manipulates a collimator or moves.

The controller 350 may control at least one among imaging option settings including a luminance setting of the examination room, a luminance setting of the X-ray irradiation region, and a color setting of the X-ray irradiation region based on an X-ray imaging condition. In an embodiment, the controller 350 may control the examination room light source 370 (see FIG. 21) and the collimator light source 322 (see FIG. 21). The controller 350 may be connected by wire or wirelessly to the examination room light source 370 and/or the collimator light source 322, and may transmit an electrical control signal to the examination room light source 370 and/or the collimator light source 322.

In an embodiment, the controller 350 may change setting values of a luminance and a color of the examination room light source 370 (see FIG. 21) and/or the collimator light source 322 (see FIG. 21) based on a difference between the luminance of the examination room and the luminance of the X-ray irradiation region. In an embodiment, the controller 350 may change setting values of a luminance and a color of the examination room light source 370 and/or the collimator light source 322 according to a position of the user or a behavior of the user who adjusts the collimator. In an embodiment, the controller 350 may change a color of LED light of the collimator light source 322 when it is determined that the color of the object is similar to the color of the ambient area of the object.

The above-described embodiments may be implemented as an executable program, and may be executed by a general-purpose digital computer that runs the program by using a non-transitory computer-readable recording medium.

Examples of the non-transitory computer-readable medium include storage media such as magnetic storage media (e.g., read only memories (ROMs), floppy discs, or hard discs), optically readable media (e.g., compact disk-read only memories (CD-ROMs), or digital versatile disks (DVDs)), etc.

The foregoing embodiments and advantages are merely exemplary and are not to be construed as limiting. The present teaching can be readily applied to other types of apparatuses. Also, the description of the embodiments is intended to be illustrative, and not to limit the scope of the claims, and many alternatives, modifications, and variations will be apparent to those skilled in the art.

What is claimed is:

1. An X-ray apparatus for controlling a position of an X-ray emitter, the X-ray apparatus comprising:
   an image obtainer configured to obtain an image of an object by photographing the object;
   an image processor configured to identify a candidate region of the object and a central point of the object by performing image processing on the obtained image, and generate a thumbnail image by causing user interfaces (UIs) indicating an irradiation region shape of the X-ray emitter and a central point of the X-ray emitter to overlap the identified candidate region of the object and the identified central point of the object, the candidate region being a region of the object to be X-rayed;
   a display configured to display the thumbnail image; and
   a controller configured to calculate the irradiation region shape of the X-ray emitter and the position of the X-ray emitter by matching the candidate region of the object and the central point of the object with the irradiation region of the X-ray emitter and the central point of the X-ray emitter, respectively, and control the position of the X-ray emitter based on the matched irradiation region of the X-ray emitter and the matched central point of the X-ray emitter.

2. The X-ray apparatus of claim 1, wherein a plurality of irradiation regions of the X-ray emitter and a plurality of central points of the X-ray emitter to be matched with the candidate region of the object and the central point of the object are provided, and
   wherein the image processor is further configured to generate a plurality of thumbnail images by causing each of the plurality of irradiation regions of the X-ray emitter and each of the plurality of central points of the X-ray emitter to overlap the obtained image.

3. The X-ray apparatus of claim 2, wherein the display is further configured to display the plurality of thumbnail images, and
   the X-ray apparatus further comprises:
   a user input receiver configured to receive a user input that selects one among the plurality of thumbnail images displayed on the display; and
   a driver configured to adjust the plurality of irradiation regions of the X-ray emitter and the position of the X-ray emitter based on the user input.

4. The X-ray apparatus of claim 3, wherein the user input receiver comprises:
   a touch screen which is embodied in the display and configured to receive a touch input of a user that touches the one among the plurality of thumbnail images displayed on the display.

5. The X-ray apparatus of claim 1, wherein the image processor is further configured to convert the irradiation region shape of the X-ray emitter and the central point of the X-ray emitter into virtual graphical user interfaces (UIs), and
   the display is further configured to display the virtual graphical UIs so that the virtual graphical UIs overlap the obtained image.

6. The X-ray apparatus of claim 1, wherein the display is further configured to display a UI that displays the central point of the object as a first marker and displays the central point of the X-ray emitter as a second marker.

7. The X-ray apparatus of claim 6, wherein a position of the second marker is corrected based on a user input.

8. The X-ray apparatus of claim 1, wherein the controller is further configured to identify a user who uses the X-ray apparatus and obtains setting information about the irradiation region of the X-ray emitter and the central point of the X-ray emitter, and
   the image processor is further configured to generate the thumbnail image based on the setting information corresponding to the identified user.

9. The X-ray apparatus of claim 8, further comprising a storage device configured to store the setting information about the irradiation region of the X-ray emitter and the central point of the X-ray emitter that is input by the user,
   wherein the image processor is further configured to obtain information about the irradiation region of the X-ray emitter and the central point of the X-ray emitter by analyzing the setting information stored in the storage device.

10. A method of controlling a position of an X-ray emitter, the method comprising:
    obtaining an image of an object by photographing the object;

identifying a candidate region of the object and a central point of the object by performing image processing on the obtained image;

calculating an irradiation region shape of the X-ray emitter and the position of the X-ray emitter by matching the identified candidate region of the object and the identified central point of the object with the irradiation region of the X-ray emitter and the central point of the X-ray emitter, respectively, the candidate region being a region of the object to be X-rayed;

generating a thumbnail image by causing information about the calculated irradiation region shape of the X-ray emitter and the calculated position of the X-ray emitter to overlap the obtained image; and displaying the thumbnail image.

11. The method of claim 10, wherein a plurality of irradiation regions of the X-ray emitter and a plurality of central points of the X-ray emitter to be matched with the candidate region of the object and the central point of the object are provided, and the generating the thumbnail image comprises generating a plurality of thumbnail images by causing each of the plurality of irradiation regions of the X-ray emitter and each of the plurality of central points of the X-ray emitter to overlap the obtained image.

12. The method of claim 11, wherein the displaying the thumbnail image comprises displaying the plurality of thumbnail images, and the method further comprises:

receiving a user input that selects one among the plurality of thumbnail images on the display; and adjusting the irradiation region of the X-ray emitter and the position of the X-ray emitter based on the user input.

13. The method of claim 10, wherein the generating the thumbnail image comprises:

converting the candidate region of the object and the central point of the object into virtual graphics; and displaying a user interface (UI) so that the virtual graphics overlap the obtained image.

14. The method of claim 10, wherein the displaying the thumbnail image comprises:

displaying a user interface (UI) that displays the central point of the object as a first marker and displays the central point of the X-ray emitter as a second marker.

15. The method of claim 10, wherein the generating the thumbnail image comprises:

identifying a user who uses the X-ray emitter; and generating the thumbnail image based on setting information about the irradiation region of the X-ray emitter and the central point of the X-ray emitter that is provided by the identified user.

* * * * *